US007498361B2

(12) United States Patent
Fogel

(10) Patent No.: US 7,498,361 B2
(45) Date of Patent: *Mar. 3, 2009

(54) METHODS OF TREATING TARDIVE DYSKINESIA AND OTHER MOVEMENT DISORDERS

(75) Inventor: Barry S. Fogel, Waban, MA (US)

(73) Assignee: Synchroneuron, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,244

(22) Filed: Jun. 27, 2001

(65) Prior Publication Data

US 2002/0013366 A1   Jan. 31, 2002

Related U.S. Application Data

(60) Division of application No. 09/193,892, filed on Nov. 18, 1998, now Pat. No. 6,294,583, which is a continuation-in-part of application No. 09/006,641, filed on Jan. 13, 1998, now Pat. No. 5,952,389.

(51) Int. Cl.
*A61K 31/13* (2006.01)
*A61K 31/045* (2006.01)
*A61K 31/04* (2006.01)

(52) U.S. Cl. ................... 514/665; 514/665; 514/724; 514/742

(58) Field of Classification Search ............... 424/289, 424/303; 514/665, 226, 327, 212, 724, 742
See application file for complete search history.

(56) References Cited

U.S. PATENT DOCUMENTS

| | | | |
|---|---|---|---|
| 4,122,193 A | | 10/1978 | Scherm et al. |
| 4,233,229 A | | 11/1980 | Chakrabarti |
| 4,355,043 A | * | 10/1982 | Durlach ...................... 514/494 |
| 4,582,705 A | * | 4/1986 | Primes et al. ............... 424/632 |
| 5,061,703 A | * | 10/1991 | Bormann et al. ....... 514/212.01 |
| 5,262,162 A | | 11/1993 | Bormann et al. |
| 5,382,601 A | | 1/1995 | Nürnberg et al. |
| 5,455,279 A | | 10/1995 | Lipton |
| 5,474,990 A | * | 12/1995 | Olney ....................... 514/226.2 |
| 5,602,150 A | * | 2/1997 | Lidsky ........................ 514/327 |
| 5,614,560 A | | 3/1997 | Lipton |
| 5,952,389 A | | 9/1999 | Fogel |

OTHER PUBLICATIONS

Review Drug Addiction. Part III. Pharmacotherapy of Addiction, Polish Journal of Pharmacology, 2001, vol. 53, pp. 415-434.*
NMDA Receptor Complex Blockade by Oral Administration of Magnesium: Comparison with MK-801, 1997, Pharmacology Biochemistry and Behavior, vol. 58, No. 1, pp. 261-268.*
Vetulani. Review Drug Addiction. Part 111. Pharmacology of Addiction, Polish Journal of Pharmacology, 2001. vol 53. pp. 415-434.
G. Bartholini. *Medicinal Research Reviews*. 5(1):55-75 (1985).

Berton et al. *Alcoholism: Clinical and Experimental Research*. 22(1):183-191 (1998).
Alexander, et al., "Serum Calcium and Magnesium in Schizophrenia: Relationship to Clinical Phenomena and Neuroleptic Treatment", Brit. F. Psychiat. 133: 143-49, 1978.
Ananth, et al., "Meige's Syndrome Associated with Neuroleptic Treatment", Am J. Psychiatry 145:4, Apr. 1988.
Andrew, "Clinical Relationship of Extrapyramidal Symptoms and Tardive Dyskinesia", Can. J. Psych., 39:576-580, 1994.
Andreassen, et al., "Tardive Dyskinesia: Behavorial Effects of Repeated Intracerebroventricular Haloperidol Injections in Rats Do Not Confirm the Kindling Hypothesis", Pharmacology Biochemistry and Behavior, 49:2, 309-312, 1994.
Andreassen, et al., "Inhibition by Memantine of the Development of Persistant Oral Dyskinesias Induced by Long-Term Haloperidol Treatment of Rats", British Journal of Pharmacology 119: 751-757, 1996.
Arthurs, et al., "Treatment of Blepharospasm with medication, Surgery and Type A Botulinum Toxin", Can J. Ophthalmol, 22:1, 1987.
Athanassenas, et al., "Serum Calcium and Magnesium Levels in Chronic Schizophrenics", Journal of Clinical Psychopharmacology, 3:4, Aug. 1983.
Bezchilbynk-Butler et al., "Antiparkinsonian Drugs in the Treatment of Neuroleptic-Induced Extrapyramidal Symptoms", Can. J. Psych., 39:74-84, 1994.
Boumans et al., "Is the Social Acceptability of Psychiatric Patients Decreased by Orofacial Dyskinesia?", Schizo Bull, 20:339-344, 1994.
Britton, et al., "Dextromethorphan Protects Against Cerebral Injury Following Transient, But Not Permanent, Focal Ischemia in Rats" Life Sciences, 60:20, 1729-1740, 1997.
Büchel et al., "Oral Tardive Dyskinesia: Validation of a Measuring Device Using Digital Image Processing", Psychopharmacology-Berl, 117:162-165, 1995.
Casey, D. "Pharmacology of Blepharospasm-Oromandibular Dystonia Syndrome", Neurology, 30:690-695, Jul. 1980.
Cassady, et al., "Neuroleptic Induced Movement Disorders", Cambridge, England: Cambridge University Press, 1997, pp. 454-469.

(Continued)

*Primary Examiner*—Yong S Chong
(74) *Attorney, Agent, or Firm*—Knobbe Martens Olson & Bear, LLP

(57) ABSTRACT

The present invention describes a novel treatment for movement disorders, including tardive dyskinesia, tic disorders, Tourette's syndrome, and blepharospasm, and other focal dystonias. The treatment of the present invention utilizes agents that simultaneously act as NMDA-type glutamate receptor antagonists and GABA-A receptor agonists. Preferably these two activities are characteristic of a single agent, for example acamprosate. Alternatively, separate agents having these activities can be combined and administered together. The invention also provides a third agent that acts as a non-competitive NMDA-receptor blocking agent or ion channel blocker that augments the effect of the primary treatment. A particularly preferred ion channel blocking agent is magnesium. Alternatively, magnesium can be administered alone for prevention and treatment of movement disorders.

7 Claims, No Drawings

OTHER PUBLICATIONS

Chabenat, et al., "Physicochemical, Pharmacological and Pharmacokinetic Study of a New GABAerigic Compound, Calcium Acetylhomotaurinate", Methods Find Exp Clin Pharmacol, 10:311-7, May 1988.

Chakos et al., "Incidence and Correlates of Tardive Dyskinesia in First Episode of Schizophrenia", Arch Gen Psychiatry, 53:313-319, 1996.

Chappell, et al., "Future Therapies of Tourette Syndrome", Neurologic Clinics of North America, 15:2, May, 1997.

Dabiri, et al., "Effectiveness of Vitamin E for Treatment of Long-Term Tardive Dyskinesia", Am J. Psychiatry 151:6, Jun. 1994.

Decker et al., "Amantadine Hydrochloride Treatment of Tardive Dyskinesia", October 7, New England J. Med, 285:860, 1971.

Delfs et al., "Expression of Glutamic Acid Decarboxylase mRNA in Striatum and Pallidum in an Animal Model of Tardive Dyskinesia", Exp. Neurol, 133:175-188, 1995.

De Mattos, et al., "Distonias Aspectos Clinicose E Terapeuticos EM 64 Pacientes", Arq. Neuropsiquiatr, 54:30-36, 1996.

Dimpfel, "Effects of Memantine on Synaptic Transmission in the Hippocampus in Vitro", Arzneimittelforschung, 45:1-5, 1995.

Durlach, et al., "Magnesium Status and Ageing: An Update", Magnesium Research 11:25-42, 1997.

Egan M.F., et al., "Treatment of Tardive Dyskinesia" Schizophr Bull, 23(4):583-609 1997.

Elston, J. "The Management of Blepharospasm and Hemifacial Spasm", J. Neurol 239:5-8, 1992.

Ema, et al., "Alcohol-Induced Vascular Damage of Brain is Ameliorated by Administration of Magnesium", Alcohol, 15:95-103, 1998.

Erdo et al., "Memantine is Highly Potent in Protecting Cortical Cultures against Excitotoxic Cell Death Evoked by Glutamate and N-Methyl-D-Aspartate", Eur. J. Pharmacol, 198:215-217, 1991.

Esper, et al., "Adult-Onset Focal Dsytonias: Presentation and Treatment Options", Tennessee Medicine, Jan. 18-20, 1997.

Fariello, R.G. et al., "Homotaurine (3 Aminopropanesulfonic Acid; 3APS) Protects Froom The Convulsant and Cytotoxic Effect of Systemically Adminstered Kainic Acid." Neurology, 32:241-5, Mar. 1982.

Galardi, et al., "Basal Ganglia and Thalamo-Cortical Hypermetabolism in Patients with Spasmodic Torticollis", Acta Neurol Scand 94:172-176, 1996.

Gao et al., "Tiagabine Inhibits Haloperidol-Induced Oral Dyskinesias in Rats", J. Neural Transmission, 95:63-69, 1994.

Gardos, et al., "The Treatment of Tardive Dyskinesias", Psychopharmacology, 1503-1511, 1995.

Hallett, M. "The Neurophysiology of Dystonia", Arch Neurol, 55: May, 1998.

Hayashi et al., "Prevalence of and Risk Factors for Respiratory Dyskinesia", Clin. Neuropharmacol, 19:390-398, 1996.

Holds, et al., "Facial Dystonia, Essential Bleopharospasm and Hemifacial Spasm", AFP, 43(6): 2113-2120, Jun. 1991.

Imamura et al., "Improved Preseveration with Amantadine", Abstract, No-To-Shinkei, 46:556-562, 1994.

Jacoby, et al., "Diltiazem Reduces the Contractility of Extraocular Muscles in Vitro and in Vivo", Investigative Ophthalmology & Visual Science, 31:569-576, Mar. 1990.

Jankovic, J. "Treatment of Hyperkinetic Movement Disorders with Tetrabenazine: A Double-Blind Crossover Study", Ann Neurol 11:41-47, 1982.

Jankovic, J. "Blepharospasm and Orofacial—Cervical Dystonia: Clinical and Pharmacological Findings in 100 Patients", Ann Neurol 13:402-411, 1983.

Jeste et al., "Risk of Tardive Dyskinesia in Older Patients. A Prospective Longitudinal Study of 266 Outpatients", Arch Gen Psychiatry, 52:756-765, 1995.

Keilhoff et al., "Memantine Prevents Quinolinic Acid-Induced Hippocampal Damage", Eur. J. Pharmacol, 219:451-454, 1992.

Kirov, et al., "Plasma Magnesium Levels in a Population of Psychiatric Patients: Correlations with Symptoms", Neuropsychobiology 30:73-78, 1994.

Kornhuber et al., "New Therapeutic Possibilities with Low-Affinity NMDA Receptor Antagonists", Abstract, Nervenarzt, 67:77-82, 1996.

Kurata, et al., "Meige's Syndrome During Long-Term Neuroleptic Treatment", The Japanese Journal of Psychiatry 43: 627-631, 1989.

Kurlan, R. "Treatment of Tics", Neurologic Clinics of North America, 15:2, 403-409, May, 1997.

Lam et al., Vitamin E in the Treatment of the Tardive Dyskinesia: A Replication Study, J. Nerv. Ment Dis, 182:113-114, 1994.

Latimer, "Tardive Dyskinesia: A Review", Abstract, Can J. Psych, 40:S49-54, 1995.

Leckman, et al., "Tic Disorders", The Psychiatric Clinics of North America, 20:4 839-861, Dec. 1997.

Lichter, et al., "Predictors of Clonidine Response in Tourette Syndrome: Implications and Inferences", Journal of Child Neurology 11:93-97, Mar. 1996.

Lipski, et al., A Study of Nutritional Deficits of Long-Stay Geriatric Patients, Age and Agening 22:244-255, 1993.

Lohr et al., "A Double-Blind Placebo-Controlled Study of Vitamin E Treatment of Tardive Dyskinesia", J. Clin. Psychiatry, 57:167-173, 1996.

Martin, et al., "Comparison of Inorganic Elements from Autopsy Tissue of Young and Elderly Subjects", J. Trace Elem. Electrolytes Health Dis.,5:203-211, 1991.

Mauriello, et al., "Treatment Selections of 239 Patients with Blepharospasm and Meige Syndrome over 11 Years", Br. J. Ophthamaol, 80(12):1073-1076, Dec. 1996.

Mauriello, et al., "Treatment Choices of 119 Patients with Hemifacial Spasm over 11 Years", Clinical Neurology and Neurosurgery, 98: 213-216, Aug. 1996.

Meshul, et al., "Correlation of Vacuous Chewing Movements with Morphological Changes in Rats Following 1-Year Treatment with Haloperidol", Psychopharmacology 125:238-247, 1996.

Muller et al., "Noncompetitive NMDA Receptor Antagonists with Fast Open-Channel Blocking Kinetics and Strong Voltage-Dependency as Potential Therapeutic Agents for Alzheimer's Dementia", Pharmacopsychiatry, 28:113-124, 1995.

Pahl et al., "Positron-Emission Tomography in Tardive Dyskinesia", J. Neuropsych Clin. Neurosci, 7:457-465, 1995.

Panula-Lehto E. et al., "Effects of Taurine, Homotaurine and GABA on Hypothalamic and Striataldopamine Metabolism." Naunyn Schmiedebergs Arch Pharmacol, 346:57-62, Jul. 1992.

Perlmutter, et al., "Decreased [$^{18}$F] Spiperone Binding in Putamen Idiopathic Focal Dystonia", The Journal of Neuroscience, 17:843-850, 1997.

Ploceniak, "Bruxisme et magnesium, mon experience clinique depuis 1980" Communications Libres, 91, suppII, 1990.

Raja, "The Treatment of Tardive Dyskinesia", Abstract, Schweiz Arch Neurol Psychaitr, 47: 1996.

Ransmayr, et al., "Pharmacological Study in Meige's Syndrome with Predominant Blepharospasm", Clinical Neuropharmacology, 11:68-76, 1988.

Rouhani, S. et al., "Effects of Muscimol or Homotaurine on Sleep-Wake States in Alcohol-dependent rats during Withdrawal." Pharmacol Biochem Behav, 59:955-60, Apr. 1998.

Sachdev, "Blinking-blepharospasm after long-term neuroleptic treatment", The Medical Journal of Australia, 150:341-343, Mar. 20, 1989.

Sachdev et al., "Negative Symptoms, Cognitive Dysfunction, Tardive Akathisia and Tardive Dyskinesia", Acta Psychiatr Scand, 93:451-459, 1996.

Sanberg, et al., "Nicotine for the Treatment of Tourette's Syndrome", Pharmacol. Ther. vol. 74, 21-25, 1997.

Sandyk, "Blepharospasm —Successful Treatment with Baclofen and Sodium Valproate", SA Medical Journal, 64:3 Dec. 1993.

Sano et al., "A Controlled Trial of Selegiline, Alpha-Tocopherol, or Both as Treatment for Alzheimer's Disease", The New England Journal of Medicine, vol. 336, No. 17, pp. 1216-1247, Apr. 24, 1997.

Scahill, et al., "Fluoxetine Has No Marked Effect on Tic Symptoms in Patients with Tourette's Syndrome: A Double-Blind Placebo-Controlled Study", Journal of Child and Adolescent Psychopharmacology, 7:75-85, 1997.

Schulz et al., "Neuroprotective Strategies for Treatment of Lesions Produced by Mitochondrial Toxins: Implications for Neurodegenerative Diseases", Neuroscience, 71:1043-1048, 1996.

Shane, et al., "Magnesium Deficiency in Alcohol Addiction and Withdrawal", Magnes Trace Elem, 92:263-268, 1991.

Silver et al., "No Difference in the Effect of Biperiden and Amantadine on Parkinsonian-and Tardive Dyskinesia-type Involuntary Movements: A Double-Blind Crossover, Placebo-Controlled Study in Medicated Chronic Schizophrenic Patients", Abstract, J. Clin. Psychiatry, 56:167-170, 1995.

Silver, et al., Case Study: Long-Term Potentiation of Neuroleptics with Transdermal Nicotine in Tourette's Syndrome, J. Am. Chil. Adolesc. Psychiatry, 35:12, Dec. 1996.

Stoessl, "Effects of Ethanol in a Putative Rodent Model of Tardive Dyskinesia", Pharmacol Biochem Behav, 54:541-546, 1996.

Steingard, Adjunctive Clonazepam Treatment of Tic Symptoms in Children with Comorbid Tic Disorders and ADHD, J. Am. Acad. Child Adolesc. Psychiatry, 33:3, Mar./Apr. 1994.

Swartz, "Tardive Psychopathology", Neuropsychobiology, 43:115-119, 1995.

Tirelli et al., "Differential Effects of Direct and Indirect Dopamine Agonists on the Induction of Gnawing in C57B1/6J Mice", J. Pharmacol Exp. Ther., 273:7-15, 1995.

Trube, et al., "Dextromethorphan: Cellular Effects Reducing Neuronal Hyperactivity" Epilepsia. 35:5 S62-S67, 1994.

Tsai, et al., "Markers of Glutamatergic Neurotransmission and Oxidative Stress Associated with Tardive Dyskinesia", Am J. Psychiatry 155:9, Sep. 1998.

Vale et al., "Amantadine for Dyskinesia Tarda", New Eng. J. Med., 284:673, 1971.

Van-Rekum et al., "N of 1 Study: Amantadine for the Amotivational Syndrome in a Patient with Traumatic Brain Injury", Brian Inj. 9:49-53, 1995.

Waddington et al., "Cognitive Dysfunction in Chronic Schizophrenia Followed Prospectively Over 10 Years and Its Longitudinal Relationship to the Emergence of Tardive Dyskinesia", Psychol Med, 26:681-688, 1996.

Wenk et al., "MK-801, Memantine and Amantadine Show Neuroprotective Activity in the Nucleus Basalis Magnocellularis", Eur. J. Pharmacol, 293:267-270, 1995.

Wilde, et al., "Acamprosate", Adis Drug Evaluation, 53:1038-1053, Jun. 1997.

Yassa, et al., "Plasma Magnesium in Chronic Schizophrenia", Int. Pharmacopsychiat. 14:57-64 (1979).

Ziemann, et al., "Decreased Motor Inhibition in Tourette's Disorder: Evidence from Transcranial Magnetic Stimulation", Am J. Psychiatry, 154:1277-1284, 1997.

* cited by examiner

METHODS OF TREATING TARDIVE DYSKINESIA AND OTHER MOVEMENT DISORDERS

PRIORITY INFORMATION

The present application is a divisional of application Ser. No. 09/193,892, filed Nov. 18, 1998, now U.S. Pat. No. 6,294,583 which is a continuation-in-part of application Ser. No. 09/006,641, filed Jan. 13, 1998, now U.S. Pat. No. 5,952,389 the entire contents of which are incorporated herein by reference.

BACKGROUND OF THE INVENTION

Movement disorders affect a significant portion of the population, causing disability as well as distress. This invention concerns the treatment of several movement disorders: 1) tics, including multiple tics and Gilles de la Tourette syndrome (TS); 2) tardive dyskinesia (TD) and related movement disorders induced by exposure to neuroleptic (antipsychotic) drugs; and 3) focal dystonias, including blepharospasm Meige syndrome, torticollis, spasmodic dysphonia, and writer's cramp.

Tics are estimated to affect 1% to 13% of boys and 1% to 11% of girls, the male-female ratio being less than 2 to 1. Approximately 5% of children between the ages of 7 and 11 years are affected with tic behavior (Leckman et al., *Neuropsychiatry of the Bas. Gang*, December, 20(4): 839-861, 1997). The estimated prevalence of multiple tics with vocalization, i.e. Tourette's syndrome, varies among different reports, ranging from 5 per 10,000 to 5 per 1,000. Tourette's syndrome is 3-4 times more common in boys than girls and 10 times more common in children and adolescents than in adults (Leckman et al., supra; Esper et al, *Tenn. Med.*, January, 90:18-20, 1997).

Tardive dyskinesia (TD) affects approximately 15-20% of patients treated with neuroleptic drugs (Khot et al., *Neuroleptics and Classic Tardive Dyskinesia*, in Lang A E, Weiner W J (eds.): *Drug Induced Movement Disorders*, Futura Publishing Co., 1992, pp 121-166). Therefore, the condition affects hundreds of thousands of people in the United States alone. The cumulative incidence of TD is substantially higher in women, in older people, and in those being treated with neuroleptics for conditions other than schizophrenia, such as bipolar disorder (manic-depressive illness) (see, e.g., Hayashi et al., *Clin. Neuropharmacol*, 19:390, 1996; Jeste et al., *Arch. Gen. Psychiatry*, 52:756, 1995). Unlike the of the acute motor side effects of neuroleptic drugs, TD does not respond in general to antiparkinson drugs (Decker et al., *New Eng. J Med.*, October 7, p. 861, 1971).

Focal dystonias are a class of related movement disorders involving the intermittent sustained contraction of a group of muscles. The most common is spasmodic torticollis, which involves twisting of the neck. Other examples are blepharospasm, which involves involuntary eye closure, and writer's cramp, which involves contraction of the muscles of the hand. The prevalence of focal dystonias in one US county was estimated as 287 per million (Monroe County Study); this suggests that at least 70,000 people are affected in the US alone.

Tardive dyskinesia (TD) is a chronic disorder of the nervous system, characterized by involuntary, irregular rhythmic movements of the mouth, tongue, and facial muscles. The upper extremities also may be involved. These movements may be accompanied, to a variable extent, by other involuntary movements and movement disorders. These include rocking, writhing, or twisting movements of the trunk (tardive dystonia), forcible eye closure (tardive blepharospasm), an irresistible impulse to move continually (tardive akathisia), jerking movements of the neck (tardive spasmodic torticollis), and disrupted respiratory movements (respiratory dyskinesia). The vast majority of TD cases are caused by the prolonged use of antipsychotic drugs (neuroleptics). A relatively small number are caused by the use of other medications, such as metoclopramide, that, like neuroleptics, block dopamine receptors. TD often manifests or worsens in severity after neuroleptic drug therapy is discontinued. Resumption of neuroleptic therapy will temporarily suppress the involuntary movements, but may aggravate them in the long run.

TD is also associated with a variable degree of cognitive impairment. Cognitive dysfunction associated with TD may involve attention, concentration, memory, or executive functions such as judgment or abstract reasoning. (see, e.g., Sachdev et al., *Acta Psychiatr Scand* 93:451, 1996; Waddington & Youssef, *Psychol. Med.* 26:681, 1996; Swartz, *Neuropsychobiology* 32:115, 1995). The cognitive impairment associated with TD usually is seen as a marker of underlying differences in brain function that predispose the patient to TD. However, it may also be due to the TD itself, and may be either irreversible, or partially reversible if the TD is successfully treated.

The pathophysiology of TD has not been established definitively. It is well known that blockade of dopamine receptors will lead to an increased number of dopamine receptors, and therefore to an increased sensitivity to dopamine of striatal neurons. (see e.g., Andrews, *Can J Psych* 39:576, 1994; Casey, in *Psychopharmacology: The Fourth Generation of Progress*, Raven Press, 1995). The first major hypothesis about the pathophysiology of TD was that TD was the result of this hypersensitivity of striatal neurons to dopamine. In support of the "dopamine supersensitivity" hypothesis, it is noted that dopamine agonists can aggravate the disorder (Bezchibnyk-Butler & Remington, *Can J. Psych.*, 39:74, 1994). However, the dopamine supersensitivity hypothesis is not compatible with the observation that TD and Parkinsonism (a dopamine deficiency state) infrequently exist together in the same patient.

Other studies have suggested that irreversible cases of TD may be related to excitotoxic damage to the basal ganglia (Andreassen & Jorgensen, *Pharmacol. Biochem. Behav.*, 49(2):309-312, 1994; Tsai et al.,: *Am J Psych*, September 155:9, 1207-13, 1998). An acquired deficiency of the inhibitory neurotransmitter GABA has also been implicated in the development of TD (Delfs et al. *Experimental Neurol.*, 133: 175-188, 1995).

A widely-studied animal mode of TD, that of vacuous chewing movements (VCM) in rats, has also yielded evidence for a glutamate-based excitotoxic mechanism in the development of the disorder (Meshul et al; *Psychopharmacology* (Berl), 125:238-47, 1996 Jun.; Andreassen et al; *Br J Pharmacol*, 199:751-7, 1996 Oct.) When administered to rats with VCM, ethanol acutely decreases the animals' orofacial movements. This effect is prevented if the rats are pre-treated with a benzodiazepine inverse agonist, suggesting that it is mediated by stimulation of GABA-A receptors by ethanol (Stoessl, *Pharmacol. Biochem. Behav.* July, 54:541-6, 1996 Jul.) Stoessl suggests that "GABAergic stimulation" deserves further investigation in the treatment of TD. He does not, however, advance the idea of treating TD with combined GABA agonism and NMDA antagonism, nor suggest using acamprosate as a treatment for TD.

The physical manifestations of TD can resemble movement disorders associated with degenerative diseases such as Huntington's disease and Parkinson's disease. Patients with TD can show chorea (quick, irregular movements of the extremities) indistinguishable from that seen in cases of Huntington's disease. Neck, trunk and limb movements of TD can be indistinguishable from those of the "peak-dose dyskinesia" associated with prolonged treatment of Parkinson's disease with levodopa.

Recent research suggests that Vitamin E can reduce symptoms of TD modestly (Lohr & Caliguiri, *J Clin Psychiatry* 57;167, 1996; Dabiri et al. *Am. J Psychiatry*, June, 151(6): 925-926, 1994). GABA agonists such as baclofen and various benzodiazepines have also been the subject of some positive reports and are widely used in practice to ameliorate the symptoms of TD, probably because their low toxicity justifies their use despite their limited efficacy. (Gardos & Cole, Psychopharmacology: The Fourth Generation of Progress, eds. Bloom and Kupfer, pp. 1503-1510, 1995). This review only cited reports of variable benefits associated with other agents including propranolol, clonidine, cholinergic agonists, buspirone and calcium-channel antagonists. However, none of these has become a generally accepted treatment for either the movement or cognitive disorders associated with TD.

In U.S. Pat. No. 5,602,150, by Lidsky et al., it was proposed that co-administration of taurine or taurine derivatives together with neuroleptics, might prevent the emergence of tardive movement disorders, on the theory that the latter are due to excitotoxic damage against which taurine would protect. The recommendation of taurine is based on studies in a single animal model. The experiments reported do not deal with any therapeutic effects of taurine on established movements, either in the presence of continued neuroleptic therapy or otherwise.

Neither the patent nor the experiments cited in it predict or imply that taurine or derivatives will be beneficial for established movement disorders. Moreover, the mechanism proposed by Lidsky et al., (supra) is based on long-term neuroprotection. He neither asserts, infers, or suggests that taurine or derivatives might have any immediate, short term effect on movement disorders.

In co-pending, commonly-owned applications Ser. Nos., 08/861,801 and 09/006,641, incorporated herein by reference, treatments with memantine (a congener of amantadine and a N-ethyl-D-aspartate type (NMDA) receptor blocker as well as a dopamine agonist), and acamprosate (a calcium salt of a derivative of the amino acid taurine and a NMDA-type receptor blocker as well as a agonist), were advanced as effective treatments for both the movement and cognitive disorders associated with TD, and were reported to be dramatically effective in several severely affected individuals.

A tic is an abrupt repetitive movement, gesture, or utterance that often mimics a normal type of behavior. Motor tics include movements such as eye blinking, head jerks or shoulder shrugs, but can vary to more complex purposive appearing behaviors such as facial expressions of emotion or meaningful gestures of the arms and head. In extreme cases, the movement can be obscene (copropraxia) or self injurious. Phonic or vocal tics range from throat clearing sounds to complex vocalizations and speech, sometimes with coprolalia (obscene speech) (Leckman et al., supra). Tics are irregular in time, though consistent regarding the muscle groups involved. Characteristically, they can be suppressed for a short time by voluntary effort.

Gilles de la Tourette syndrome (TS) is the most severe tic disorder. Patients with TS have multiple tics, including at least one vocal (phonic) tic. TS becomes apparent in early childhood with the presentation of simple motor tics, for example, eye blinking or head jerks. Initially, tics may come and go, but in time tics become persistent and severe and begin to have adverse effects on the child and the child's family. Phonic tics present, on average, 1 to 2 years after the onset of motor tics. By the age of 10, most children have developed an awareness of the premonitory urges that frequently precede a tic. Such premonitions may enable the individual to voluntary suppress the tic, yet premonition unfortunately adds to the discomfort associated with having the disorder. By late adolescence/early adulthood tic disorders can improve significantly in certain individuals. However, adults who continue to suffer from tics often have particularly severe and debilitating symptoms. (Leckman et al., supra).

The pathophysiology of tic disorders like, that of TD, has not yet been established, although several plausible hypotheses have been set forth. Excessive activity of a cortical-triatal-pallidal-thalamic-cortical sensorimotor loop has been implicated in the lack of motor impulse control associated with tic disorders (Ziemann et al., *Am. J Psychiatry*, Vol 154, September, 1997; Leckman et al., supra). This hyperactivity may reflect excessive dopaminergic activity in the striatum, or a relative deficiency of inhibitory transmission. —While dysfunction of the basal ganglia or their connections is likely to be present, the basal ganglia, thalamus, and motor cortex are anatomically normal in most cases.

Patients with moderate to severe motor and vocal tics are likely to require drug therapy. Many classes of neurological and psychiatric medications have been tried, but only neuroleptics, alpha-2 adrenergic agonists, and clonazepam have attained the status of standard treatments. (For recent reviews see Chappell et al., *Neur. Clin. of North Am.*, 15(2), May 1997; Kurlan, *Neurol. Clin.*, May, 15:403-409, 1997; Lichter et al., *J Child Neur.*, 11(2), March, 1996; Leckman et al., supra; Esper et al, *Tenn. Med.*, January, 90:18-20, 1997; Scahill et al., *J Child Adolesc Phychopharcmacol*, 7(2), 1997; incorporated herein by reference). Unfortunately, all three of the commonly-used treatment for TS have significant drawbacks.

The most common therapies used for the treatment of tic disorders are the neuroleptics (i.e. dopamine antagonist antipsychotic drugs). Within this category, haloperidol and pimozide are most often used in the United States. Neuroleptic treatment usually will suppress the involuntary movements of tic disorders, with up to 85% of patients experiencing relief-(Esper et al., supra). The side effects of neuroleptic drugs include sedation, depression, parkinsonism, cognitive impairment, and tardive dyskinesia. Other tardive movement disorders can develop with prolonged use. The intolerability of side effects often leads patients to discontinue neuroleptic therapy for TS, while the risk of TD makes most physicians unwilling to use them in milder cases. Those with more severe TS must often make an unpleasant choice between distressing symptoms and distressing side effects. People with simple tics may experience emotional distress, embarrassment, impaired self-esteem, or physical injury if their tics are sufficiently violent. Yet, they usually will not be treated with neuroleptics because their side effects and long-term toxicity that are not acceptable in the treatment of relatively mild cases.

Other drug treatments for TS do not carry the risk of TD. But they are less efficacious than neuroleptics. The most common non-neuroleptic alternatives are alpha-2 adrenergic agonists such as clonidine. Unfortunately, fewer than 50% (perhaps as few as 25%) of patients treated with clonidine show clinically significant improvement of tic-related symptoms (Esper et al., supra; Chappell et al., supra). Further, many patients whose tics do respond to clonidine will have side effects that limit its use, most often hypotension or sedation.

Another non-neuroleptic treatment, clonazepam, a benzodiazepine with GABA-A and serotonergic actions, has some efficacy in the treatment of Tourette's syndrome (Steingard et al., *J. Am Acad Child Adolesc Psychiatry*, March-April, 33:394-9, 1994). Sedation and ataxia limit the dosage of clonazepam; the tolerable dose often is below that needed to suppress the patient's tics.

A new class of compounds that act as antagonists of brain serotonergic 5-$HT_2$ receptors initially showed promising results, although children and adolescents experience increase in sensitivity to side effects. (Chappell et al., supra). Additional alternatives that have received recent attention include antioxidant treatment (Rotrosen et al., *Prost. Leuk. and Ess. Fatty Acids*, 55(1 & 2), 1996), transcranial magnetic stimulation (Ziemann et al., supra), nicotine treatment (Sanberg et al., *Pharmacol. Ther.*, 74(1)., 1997; Silver et al., *J. Am. Acad. Adolesc. Psychiatry*, Vol 35, December, 1996) and botulinum toxin treatment (Esper et al., supra). While each of these treatments has offered clinically significant relief to individual patients, none has replaced neuroleptics as the treatment of choice. Clearly, there is a need for additional treatments for tics and TS that do not carry the side effects and long term risks of neuroleptics.

It has been suggested, on theoretical grounds, that future therapies for Tourette's syndrome might include glutamate antagonists, although a recent article proposing their use makes no mention of any specific drugs that might fulfill this role (Chappell et al., *Neurol. Clin.* May, 15(2):429-450, 1997). 4).

A focal dystonia is a recurrent abnormal posturing of some part of the body. The spasms of focaldystonia can last many seconds at a time, causing major disruption of the function of the affected area. Some of the focal dystonias are precipitated by repetitive movements; writer's cramp is the best known example. Focal dystonia can involve the face (e.g., blepharospasm, mandibular dystonia), the neck (torticollis), the limbs (e.g., writer's cramp), or the trunk. Dystonia can occur spontaneously or can be precipitated by exposure to neuroleptic drugs and other dopamine receptor blockers (tardive dystonia). No systemic drug therapy is generally effective, but some drugs give partial relief to some patients. Those most often prescribed are anticholinergics, baclofen, benzodiazepines, and dopamine agonists and antagonists. The most consistently effective treatment is the injection of botulinum toxin into affected muscles.

Positron emission tomography has shown that one specific dystonia, torticollis, is associated with neuronal hypermetabolism in the basal ganglia. It has been hypothesized that hyperactivity of a motor control loop involving the cerebral cortex, basal ganglia, and thalamus is responsible for the abnormal postures and movements (i.e. movements into and out of abnormal postures) characteristic of dystonia (Galardi et al., *Acta. Neurol Scand*, September, 94:172-6, 1996). Other studies have shown abnormal dopaminergic transmission or receptor function in patients with dystonia (see, e.g. Perlmutter et al., *J Neurosci*, January 15, 17:843-50, 1997). Of note, both too much or too little dopamine may be associated with dystonia, since patients with Parkinson's disease and dystonia can have the problem both at peak and trough levels of levodopa (Hallett, *Arch. Neurol*. May, 55:601-3, 1998). It is evident that similar mechanisms may be involved in the pathophysiology of tic disorders and focal dystonias.

The various focal dystonias tend to respond to the same drugs (Chen, *Clin. Orthop*, June, 102-6, 1998; Esper et al; *Tenn. Med*, January, 90:18-20, 1997; De Mattos et al., *Arq. Neuropsychiatry*, March 54:30-6, 1996) This suggests that a new treatment helpful for one focal dystonia would be likely to be helpful for another. Furthermore, the common symptoms, signs, and responses to medication of spontaneous (idiopathic) dystonia and neuroleptic-induced dystonia suggest that an effective treatment for a drug-induced focal dystonia will be effective for the same dystonia occurring spontaneously.

Blepharospasm, one of the focal dystonias, is a condition that involves continually recurring involuntary eye closure or excessive forceful blinking. Blepharospasm is one of the most common disorders of oculomotor function. It is variably regarded as a facial dyskinesia or a facial dystonia. When it occurs together with dystonia of the oral and mandibular regions, with or without involvement of the neck, it is referred to as Meige syndrome. Blepharospasm can significantly impair visual function. Patients can become unable to read, to drive an automobile, or to do any skilled work requiring visual control. Blepharospasm can occur spontaneously (idiopathic blepharospasm) and with a prevalence that increases with increasing age; most cases arise in the fifth and sixth decades of life (Holds et al., *Am. Fam. Physician*, June, 43:2113-20, 1991). It also can occur as a sequel to neuroleptic drug treatment (Ananth et al., *Am. J Psychiatry*, April, 145: 513-5, 1988; Kurata et al., *Jpn. J. Psychiatry. Neurol.*, December, 43:627-31, 1989; Sachdev et al., *Med. J. Aust.*, March 20, 150:341-3, 1989) and perhaps treatment with other classes of psychotropic drugs (Mauriello et al., *J Neuropathol*, June, 18:153-7, 1998), either alone or in conjunction with tardive dyskinesia or tardive dystonia. Another report of 19 patients with severe tardive dyskinesia, stated that frequent eye blinking was the most frequent prodromal sign of the disorder (Gardos et al., supra, 1988). The oculomotor phenomena of idiopathic blepharospasm and Meige syndrome are identical with those seen in cases induced by neuroleptic treatment. Differences between idiopathic blepharospasm and tardive blepharospasm do not involve the ocular movements themselves. Patients with idiopathic blepharospasm are more likely to have a family history of movement disorders, and those with tardive blepharospasm are more likely to have movements of other parts of the body.

Though many substances have been tested for their ability to relieve blapharospasm, injection of botulinum toxin into orbicularis oculi muscles is the mainstay of treatment (Mauriello et al., Br. J. Ophthalmol, December, 80:1073-6, 1996). These injections weaken the muscles responsible for eye closure, thereby mitigating the involuntary movements of those muscles. They may also indirectly influence oculomotor control by the central nervous system, by altering the input from motor nerve afferents. Botulinum toxin injections have become treatment of choice because of the limited efficacy of the numerous systemic drug treatments tried to date.

Movements associated with blepharospasm "do not respond to systemic drug treatment". In one large case series, only 22% of blepharospasm patients treated with systemic medications got "marked and persistent relief" (Jankovic et al., *Mov. Disord.*, May, 9:347-349, 1983). In another report, of the 13 patients with blepharospasm who did not do well with botulinum toxin injections, only 2 showed any improvement when given systemic drug therapy (Mauriello et al., *Clin. Neurol. Neurosurg.*, August, 98:213-6, 1996)). Even botulinum toxin injections are not always efficacious. Surgery is sometimes recommended for patients who do not get relief from botulinum toxin injections (Elston et al., *J. Neurol*, January, 239:5-8, 1992).

Of the systemic treatments, (see, for example, Arthurs et al., *Can. J. Ophthalmol*; February, 22:24-8, 1987; Casey et al., *Neurology*, July, 30:690-5, 1980; Jacoby et al., *Invest. Ophthalmol. Vis. Sci.*, March, 31:569-76, 1990; Michaeli et al., *Clin. Neuropharmacol.*, June, 11:241-9, 1988; Ransmayr et al., *Clin. Neuropharmacol.*, February, 11:68-76, 1988; clonazepam, a GABA agonist, was the only drug consistently found useful (Jankovic et al., *Ann. Neurol.*, April, 13:402-11, 1983). A combination of two GABA agonist agents, valproate and baclofen, was efficacious in a single case (Sandyk, et al., *S Afr Med J*, December, 64:955-6, 1983). Tetrabenazine, a dopamine depleting agent, alleviated involuntary movements in 4 of 6 patients with Meige syndrome, but the patients had many undesirable side effects including drowsiness, drooling and Parkinsonism (Jankovic, et al., *Ann Neurol*, January, 11:41-7, 1982). Because of such unpleasant side effects, tetrabenazine has not become a widely-used treatment for blepharospasm, tics or even tardive dyskinesia, despite the absence of other generally effective treatments for these conditions. In sum, though GABA agonists and dopamine receptor blockers have been employed with some benefit in the treatment of idiopathic blepharospasm, neither type of medication has proved to be a generally satisfactory treatment.

Because magnesium deficiency can cause neuromuscular excitability (Durlach et al, *Magnes Res*, June, 10:169-95, 1997), it could potentially cause or aggravate movement disorders. Ploceniak, (*Communications Libres*, 91, suppII, 1990) reported, without details, that he had found magnesium supplementation useful in patients with bruxism (teeth grinding) and facial tics associated with tetany (susceptibility to muscle cramps typical of hypocalcemia). He did not, however, suggest that magnesium supplementation would help patients with Tourette's syndrome, or those with tics not due to magnesium deficiency.

There is considerable evidence for abnormalities of magnesium status in patients with severe mental illness (see for example, Athanassenas et al., *J. Clin. Psychopharmacol.* August, 3:212-6, 1983; Alexander et al., *Br. J. Psychiatry*, August, 133:143-9, 1978; Kirov et al., *Neuropsychobiology,* 30(2-3):73-78, 1994; Wang et al, 1997; Yassa et al., *Int Pharmacopsychiatry,* 14(1):57-64, 1979). Alexander et al. (supra, 1978) found that those schizophrenic patients developing extrapyramidal side effects from neuroleptics had, on average, lower magnesium levels than those not having such side effects. Neuromuscular excitability and anxiety are common acute manifestations of magnesium depletion. And, there are theoretical reasons to speculate that magnesium deficiency may contribute to a wide range of neurodegenerative disorders (Durlach et al. 1997, supra). However there has been no suggestion that magnesium deficiency is a cause of tardive dyskinesia, tics, Tourette's syndrome or blepharospasm or that magnesium supplementation can be used to successfully treat or prevent movement disorders.

Although the present day pharmacopeia offers a variety of agents to treat movement disorders, none of these agents can prevent or cure these conditions. Furthermore, the most effective treatments are often associated with intolerable side effects. There remains a clearcut need for new treatments for TD, other tardive movement disorders, tics, Tourette's syndrome, blepharospasm, and other focal dystonias that have greater efficacy and fewer side effects than those currently available.

SUMMARY OF THE INVENTION

The present invention provides a method for treating movement disorders including tic disorders, TS, TD, and focal dystonias, in humans. In one aspect, the invention provides a method for reducing involuntary movements characteristic of patients with hyperkinetic or dyskinetic movement disorders by administering a pharmacological agent, that both (i) acts directly or indirectly as an agonist at GABA-A receptors and (ii) decreases NMDA-type glutamate neurotransmission by an indirect or modulatory mechanism. Specific instances include calcium N-acetylhomotaurinate (acamprosate), magnesium N-acetylhomotaurinate, other salts of N-acetylhomotaurinate, derivatives of N-acetylhomotaurinate with similar pharmacodynamic effects on GABA and NMDA-type glutamate neurotransmission, and pro-drugs that are metabolized in the liver, blood, or brain to yield N-acetylhomotaurinate or a derivative with similar pharmacodynamic effects. In another aspect, the present invention provides methods for reducing involuntary movements characteristic of patients with hyperkinetic or dyskinetic movement disorders by administering more than one pharmacological agent that, in combination, act to increase GABA-A receptor activity and decrease NMDA-type glutamate neurotransmission.

The present invention also provides a method for treating movement disorders by combining memantine, magnesium or a non-competitive NMDA receptor antagonist with acamprosate, another compound or mixture thereof (specifically including those enumerated in the previous paragraph) that simultaneously decreases the postsynaptic response to glutamate at NMDA-type receptors and also directly or indirectly increases GABA-A transmission. In preferred embodiments, magnesium is used as a non-competitive NMDA receptor antagonist.

The present invention demonstrates that magnesium can augment the effect of pharmacological agents used to treat movement disorders including tics and TD, and, by extension, TS and blepharospasm. Synergistic activity is shown between magnesium and pharmacological agents that act as NMDA receptor antagonists and simultaneously as enhancers of GABA-A transmission. Alternatively, magnesium alone is used to reduce symptoms associated with movement disorders.

In another preferred embodiment, supplementation with magnesium is used to prevent movement disorders in people already at risk for them, by reducing the risk, or by delaying the onset of the movement disorder for which they are at risk. In particular, it is asserted that magnesium deficiency is a risk factor for the development of TD in patients receiving neuroleptics, and that magnesium supplementation may prevent the development of TD, particularly in patients prone to magnesium deficiency, including elderly women, alcoholics, diabetics, people taking diuretics, and malnourished individuals.

In other embodiments, any combination of agents that act as NMDA receptor antagonists together with one or more agents that facilitate GABA-A neurotransmission (by acting as GABA-A receptor agonists, by increasing GABA-A release, or by increasing the post-synaptic response to GABA-A receptor stimulation), with or without magnesium, are used for treatment of movement disorders.

A pill combining agents that act as NMDA-type glutamate receptor antagonists, GABA agonists and magnesium is proposed as a specific vehicle for the delivery of this combined therapy. In addition, other oral preparations are suggested; the mixture can be delivered in a syrup, elixir, or time release capsule. The latter is suggested as a method for prolonging the duration of action of a dose of the mixture.

DEFINITIONS

"Tardive dyskinesia": As used herein "tardive dyskinesia" is meant to include tardive dystonia and other movement disorders related to long-term neuroleptic use. The abbreviation TD may be used in place of the term "tardive dyskinesia".

"Tourette's syndrome": "Tourette's syndrome" as used herein is synonymous with "Gilles de la Tourette syndromes", "Tourette syndrome", "Tourette disorder", and similar expressions. The abbreviation TS may be used in place of any of these terms.

"Blepharospasm": As used herein, "blepharospasm" includes Meige syndrome, which is a combination of blepharospasm and dystonia of the face and/or neck.

"Acamprosate": As used herein, "acamprosate" refers to calcium N-acetylhomotaurinate. These two terms may be used interchangeably. "N-acetylhomotaurinate" and "acetylhomotaurinate" are used interchangeably.

"Acamprosate and related compounds": "Acamprosate and related compounds" refers to calcium acetylhomotaurinate, magnesium acetyllhomotaurinate, other salts of N-acetylhomotaurinate, acetylhomotaurine base, homotaurine base and homotaurine salts, derivatives of homotaurine or acetylhomotaurine that have similar pharmacodynamic activity with respect to GABA-A and NMDA-type glutamate transmission, and pro-drugs that are metabolized in the blood, liver, or brain to yield acetylhomotaurinate or derivatives with similar pharmacodynamic activity with respect to GABA-A and NMDA-type glutamate transmission. Acamprosate decreases the intra cellular response of neurons stimulated by glutamate at the NMDA receptor, and enhances GABA-A transmission, at least in part by an antagonist effect on pre-synaptic GABA-B inhibitory autoreceptors. For ease of expression, I refer to acamprosate and similar compounds as: "GABA agonists and NMDA antagonists", "GABA-A Agonists and NMDA-antagonists", "agents that increase GABA transmission and decrease NMDA-type glutamate transmission", "GABA agonists and glutamate antagonists", and "up regulators of GABA transmission and down-regulators of NMDA-type glutamate transmission".

"GABA-A transmission": "GABA-A transmission" refers to the pharmacodynamic phenomena associated with the activation of GABA-A receptors by GABA. Enhancement of GABA-A transmission may involve increasing the release of GABA, decreasing its metabolism, increasing receptor binding, or increasing the cellular effects of receptor binding "GABA-A receptor agonist": "GABA-A receptor agonist", as used herein refers to molecules that are capable of binding to active or modulatory sites on the GABA-A receptor to enhance GABA-A transmission. (as defined above)

"NMDA receptor antagonist": As used herein, "NMDA receptor antagonist" is any molecule that inhibits or diminishes the postsynaptic response of NMDA-type glutamate receptors to glutamate.

"NMDA-type glutanae neurofransmission": "NMDA-type glutanate Neurotransmission" is used herein to broadly refer to anything that would decrease NMDA-glutanate transmission, whether it acts before the synapse, at the receptor binding site, within the ion channel, within the cell membrane, or inside the neuron. This includes anything that reduces release of glutanate at synapses with NMDA receptors, alters the binding of glutanate to NMDA receptors or alters the number of NMDA receptors.

"Effective": "Effective" as used herein in reference to dose refers to the administration of a specific amount of a pharmacologically active agent tailored to each individual patient manifesting symptoms of a particular movement disorder (e.g. TD, TS, other tic disorders, or blepharospasm), sufficient to cause a reduction or improvement in any of the associated symptoms (including hyperkinesia, dyskinesia or dystonia, and associated cognitive or other mental symptoms), with tolerable adverse effects. Experimentally, doses of acamprosate ranging from 333 mg to 666 mg administered three to four times daily are effective. A person skilled in the art will recognize that the optimal dose of a pharmaceutical agent administered will vary from one individual to another. Dosage in individual patients should take into account the patient's height, weight, rate of absorption and metabolism of the medication in question, and the stage of the disorder to be treated, as well as what other pharmacological agents are administered concurrently.

"Movement disorder": "Movement disorder", as used herein, is used to refer to all forms of abnormal and involuntary movements, including vocalizations. Movement disorders include, for example, tardive dyskinesia (TD), tics, Gilles de la Tourette syndrome (TS), Parkinson's disease, Huntington's disease, and focal dystonias such as blepharospasm.

"Tic disorder": "Tic disorder" as used herein, refers to an abrupt repetitive movement, gesture, or utterance that often mimics a fragment of purposeful behavior. Tics are characterized by stereotyped, repetitive, but irregularly rhythmic involuntary movements. They include both motor tics and vocal (phonic) tics. Tic disorders include, for example, simple tics, multiple tics and Gilles de la Tourette syndrome, defined as multiple tics with vocalizations.

DETAILED DESCRIPTION OF THE INVENTION

The present invention relates to prevention and treatment of movement disorders, including tic disorders, tardive dyskinesia and other related conditions. In one aspect of the present invention, I have discovered that an agent used in the treatment of abstinent alcoholics, not contemplated for use in treatment of tardive dyskinesia or other movement disorders, including Tourette's syndrome and tics, is effective in reducing the hyperkinesia and dyskinesia of patients with movement disorders. Several years ago, I hypothesized that TD represents a form of non-linear oscillation in neural circuits involving the basal ganglia, and that oscillation might be reduced by agents that block excitatory neurotransmission. PET scan studies have demonstrated increased metabolism in the globus pallidus and primary motor cortex in schizophrenic patients with TD, but not in those without TD (Pahl et al., *J Neuropsych Clin Neurosci* 7:457, 1995). This suggests that TD is associated with hyperactivity in a motor control circuit, which might be part of the putative nonlinear oscillator.

As noted above, I have advanced the hypothesis that agents which act to reduce the gain in a motor control circuit through the striatum, may have a beneficial action on TD and related movement disorders (e.g., Tourette's syndrome and tics). GABA is an inhibitory neurotransmitter in the striatum. Thus, support for my hypothesis comes from animal evidence indicating that agents that directly or indirectly stimulate GABA receptors can decrease neuroleptic-induced dyskinesias (Gao et al. *J Neural Transmission* 95:63, 1993; Stoessl, *Pharmacol.*

Biochem. Behav., 54:541, 1996). Rats with neuroleptic-induced dyskinesia demonstrate decreased striatal levels of glutamic acid decarboxylase, the rate-limiting enzyme in the production of GABA (Delfs et al., *Exp. Neurol.*, 133:175, 1995).

Without limiting the biochemical mechanism of the invention to that described here, it appears that drugs that act to reduce the gain in the hypothesized oscillator circuit would reduce the involuntary movements of tardive dyskinesia. GABA, glutamate, and dopamine are the principal neurotransmitters in the circuit. Other neurotransmitters, including norepinephrine, serotonin, acetylcholine and endogenous opiates are hypothesized to have indirect actions on the oscillator circuit. In my co-pending patent application Ser. No. 08/861,801, the teachings of which are incorporated herein by reference, I disclosed that certain antagonists of excitatory neurotransmitters are effective in treating both the movement and cognitive disorders associated with TD, tardive dystonia, and related movement disorders.

In the current invention, I disclose that acamprosate, a GABA-receptor agonist that also diminishes the postsynaptic response of NMDA-type receptors to glutamate can ameliorate TD as well as related involuntary movements and cognitive symptoms. For example, according the theory of the present invention, a GABA agonist with concurrent effects on glutamate transmission reduces the severity of the involuntary movements associated with TD. Such a GABA agonist alleviates focal dystonias, for example blepharospasm associated with TD and by extension idiopathic blepharospasm, which is likely to share a common mechanism, in light of the response of both to dopamine antagonists, to GABA agonists, and to botulinum toxin injections. To further this point, an expert on blepharospasm, Dr. Gary Borodic of the Harvard Medical School, states that neuroleptic-induced (tardive) blepharospasm is in general less responsive to medications than the spontaneous kind (Borodic, personal communication, 1998). If this is so, a treatment effective for tardive blepharospasm is especially likely to be helpful for spontaneous blepharospasm.

Likewise, treatment with acamprosate will likely ameliorate symptoms associated with Meige syndrome, which is blepharospasm accompanied by dystonic movements of the neck and lower face. Also disclosed in the present application is that acamprosate dramatically diminishes dyskinetic movements associated with tic disorders, including both single and multiple tics. Furthermore, I propose that acamprosate and other agents that both (i) decrease NMDA-type glutamate neurotransmission, and (ii) increase GABA-A receptor neurotransmission are useful in the treatment of a common and severe type of tic disorder, Tourette's syndrome, which is characterized by multiple motor and phonic tics.

Acamprosate (calcium N-acetylhomotaurinate) is the calcium salt of homotaurine, a derivative of the amino acid taurine. It is used clinically in the treatment of abstinent alcoholics to reduce or inhibit their craving for alcohol. Acamprosate, which is chemically similar to the inhibitory neurotransmitter GABA, is a GABA agonist, particularly at GABA-A receptors. Moreover, it reduces the postsynaptic response of NMDA-type glutamate receptors and reduces calcium influxes through voltage-operated channels. (Wilde & Wagstaff, *Drugs*, 53:1039-53, 1997)

Acamprosate is a particularly attractive drug for treating chronic movement disorders, because of its very low toxicity. In controlled trials for alcoholism treatment involving 3,338 patients, acamprosate had no severe medical or neurological side effects. Indeed, the rate of subject dropout was identical in the group receiving acamprosate treatment and in the group receiving a placebo (Wilde and Wagstaff, *Drugs*, June, 53(6): 1038-53, 1996). This is in stark contrast to existing systemic treatments for TD and TS. For these, as noted above, intolerable side effects are common, and impose a major limitation on their clinical utility.

The above hypothesis regarding a motor control circuit involving GABA (via GABA-A receptors) and glutamate (via NMDA receptors) implies that any drug that is a GABA agonist and an NMDA-type glutamate antagonist can ameliorate dyskinetic movements. Acamprosate (calcium N-acetylhomotaurinate) is a specific example of such a drug for which I offer direct evidence in humans of efficacy in the treatment of dyskinesia. Other examples of such drugs include other salts of N-acetylhomotaurine, derivatives of taurine and homotaurine with similar effects on GABA and NMDA-type glutamate transmission, and pro-drugs that are metabolized in the liver, blood, or brain to yield N-acetylhomotaurinate or related compounds with similar pharmacodynamic properties.

Accordingly, a preferred embodiment of the present invention provides derivatives of homotaurine and N-acetylhomotaurine effective doses to a patient for treatment of movement disorders. Particularly preferred are derivatives of acamprosate that are readily absorbed from the gastrointestinal tract. Acamprosate is irregularly absorbed from the GI tract, in part due to the polar, hydrophilic character of the acetylhomotaurinate ion. It is well known in the art that certain derivatives of drugs may be absorbed better and more reliably because they are more lipophilic. For example, esters prepared from the acetylhomotaurinate ion would be more lipophilic, and therefore might have greater and more predictable absorption through the membranes of the intestinal mucosa. If such an ester were nontoxic and naturally metabolized in the body, for example, cleaved by enzymes in the blood, liver or the brain, it would be particularly preferred as a vehicle for reliably delivering the acetylhomotaurinate ion to the brain. Furthermore, such derivatives as described above would have, in appropriate dosages, equal or greater efficacy in treating any movement disorder responsive to acamprosate. Generally, any pro-drug with improved delivery of acamprosate would be a preferred means of delivery according to the present invention. Additionally a particularly preferred form of acamprosate would be a derivative of acamprosate with a long half-life. Such a derivative of acamprosate would be clinically superior to acamprosate, because it could be taken once daily, rather than three or four times per day, as is necessary when acamprosate is used. An additional approach to lengthening the half-life of acamprosate or a related medication is to deliver it in a time-release capsule.

In other preferred embodiments, these derivatives are used to treat dyskinetic movement disorders associated with prolonged exposure to neuroleptic medications. Additionally, compositions described in the present application can be used to treat tardive dyskinesia in abstinent alcohol abusers who are treated with neuroleptics for concurrent mental disorders, for example bipolar disorder or schizophrenia. More particularly, the present invention provides treatments that reduce the severity and duration of various related movement disorders.

Another preferred embodiment of the present invention provides a treatment for focal dystonias. One example of a focal dystonia, blepharospasm, is a target for treatment in the present invention. As mentioned above, blepharospasm is a condition that involves involuntary forced eye closure. As mentioned above, blepharospasm can occur spontaneously (idiopathic blepharospasm) or can be a form of tardive movement disorder. The eye movement disorder of idiopathic blepharospasm is clinically identical to the one that arises following neuroleptic exposure and therefore might be expected to respond to the same treatments that are efficacious for tardive movement disorders. In fact, both disorders are ameliorated, at least in the short term, by neuroleptic drugs and other dopamine antagonists, and both are responsive to injections of the orbicularis oculi muscles with botulinum toxin (Casey, *Neurology*, July, 30:690-5, 1980).

The present invention demonstrates relief of blepharospasm associated with tardive dyskinesia by treatment with acamprosate, suggesting that acamprosate and related compounds and derivatives with combined action on GABA and NMDA-type glutamate receptors will benefit people with idiopathic blepharospasm and all other focal dystonias, whether spontaneous or induced by exposure to neuroleptic medications.

In one preferred embodiment of this aspect of the invention, a pharmaceutical agent is selected from the group of agents that act as GABA-receptor agonists and also act to decrease NMDA receptor function by an indirect or modulatory mechanism such as, in a non-limiting fashion, acamprosate calcium (calcium N-acetylhomotaurinate), other salts of N-acetylhomotaurinate (e.g., magnesium N-acetylhomotaurinate or lithium N-acetylhomotaurinate), acetylhomotaurine base, other homotaurine derivatives with similar pharmacodynamic actions on GABA and glutamate transmission, and pro-drugs that are metabolized in the liver, blood, or brain to yield N-acetylhomotaurinate or related compounds with similar pharmacodynamic actions on GABA and glutamate transmission. In another preferred embodiment, a pharmaceutical agent is selected from the group of agents that have the ability to reduce glutamate-produced excitatory post-synaptic potentials in striatal cells, including acamprosate and the range of similar compounds and pro-drugs described previously). In other preferred embodiments, a combination of two or more pharmaceutical agents is selected such that the combination acts concurrently to augment GABA transmission (particularly via GABA-A receptors) and to attenuate NMDA-type glutamate transmission (e.g., by noncompetitive inhibition, or by indirect or modulatory effects on NMDA receptors). A fourth embodiment is to combine such a compound or mixture of compounds with memantine or a similar non-competitive NMDA-receptor blocking agent described in detail below. The combinations may be either mixtures, covalently-bound moieties with combined action, or pro-drugs metabolized in the blood, liver, or brain to release each member of the combination.

Risk factors for TD include advanced age, diabetes, alcoholism and a primary psychiatric diagnosis of a mood disorder rather than schizophrenia. Each of these risk factors also associated with a high prevalence of magnesium deficiency (Durlach, et al., *Magnes Res*, March, 1998; G'amez et al., *Sci. Total. Environ.*, September 15, 203(3):245-51 1997; Gullestad et al., *J Am Coll Nutr*, February, 13:45-50, 1994; De Leeuw et al,. *Magnes. Res.*, June, 10:135-41, 1997; Lipski et al, *Age Ageing*, July, 22:244-55, 1993; Martin et al., *J. Trace. Elem. Electrolytes Health Dis*, September, 5:203-11, 1991; Shane et al., *Magnes. Trace. Elem.*, 10:263-8, 1991-1992; Zorbas et al., *Biol. Trace. Elem. Res.*, July-August, 58:103-16, 1997). Because people that fit the profile for being at risk for developing TD have an increased risk of magnesium deficiency, I hypothesize that magnesium deficiency (per se) is also a risk factor for tardive dyskinesia and other movement disorders. Therefore, I further assert that magnesium supplementation can alleviate or prevent movement disorders and potentiate the action of other treatments, whether or not the individual treated shows tetany or other signs of magnesium deficiency. (See Case Report 4, in which treatment for a patient with tardive dyskinesia was enhanced by adding a magnesium supplement.).

Risk of developing a movement disorder can be assessed, according to the present invention by administering to a patient a sufficient and non-toxic dose of magnesium ion (i.e. a "magnesium load") and subsequently measuring the amount of magnesium ion excreted in the patient's urine. More specifically risk of developing a neuroleptic or dopamine receptor blocker—induced movement disorder can be assessed by performing standard tests of total magnesium status. If magnesium deficiency is present, there is a greater than normal retention of magnesium load, and diminished excretion of magnesium in the urine. If an abnormally low proportion of magnesium is recovered in a 24 hour sample of the patient's urine, the patient is magnesium-deficient and at risk for developing a movement disorder.

The present invention demonstrates that supplementation with magnesium can reduce symptoms associated with a simple tic and augment the action of acamprosate in treatment of a simple tic (see Case Report 5). Furthermore, magnesium administered together with acamprosate reduces symptoms associated with simple tic better than either magnesium or acamprosate alone. Together, cases 4 and 5 suggest that supplementation with magnesium ion may be used to successfully treat other types of movement disorder.

In preferred embodiments of the present invention, magnesium is used for treatment of movement disorders (e.g., TD, Tourette's Syndrome, and focal dystonias particularly blepharospasm). In addition, magnesium supplementation can be used to reduce the risk of developing a movement disorder. In one preferred embodiment, movement disorders may be prevented by magnesium supplementation. In another embodiment, magnesium supplementation may delay the onset of a movement disorder in a person identified as being at risk for developing a movement disorder. In yet another embodiment, supplementation with magnesium will reduce the symptoms associated with various movement disorders.

According to the present invention magnesium supplementation will augment the therapeutic effects of other NMDA-type receptor antagonists and down-regulators (see Case Report 5). In one preferred embodiment, magnesium is administered with acamprosate (calcium N-acetylhomotaurine) to treat TD and other movement disorders resulting from neuroleptic drug use, tics, Tourette' syndrome, blepharospasm, other focal dystonias, and the peak-dose dyskinesia of Parkinson's disease. In a particularly preferred embodiment, the magnesium salt of N-acetylhomotaurine and the magnesium salts of those derivatives of N-acetylhomotaurine that similarly enhance GABA transmission and diminish NMDA-glutamate neurotransmission, are effective treatments for movement disorders.

It will be recognized by those skilled in the art that all conditions for which N-acetylhomotaurine is an effective treatment, the magnesium salt of N-acetylhomotaurine, and the magnesium salts of those derivatives of N-acetylhomotaurine that have similar effects on GABA neurotransmission and NMDA-glutamate neurotransmission will also be effective treatments. Alternatively, any magnesium salt may be administered with any salt of those derivatives of N-acetylhomotaurine to treat hyperkinetic and dyskinetic movement disorders. In one non-limiting example, a pill containing the appropriate dose of acamprosate together with the appropriate dose of magnesium may be formulated and administered to a patient with a movement disorder. In other preferred embodiments, an agent that has NMDA antagonist activity and GABA agonist activity is combined with the appropriate dose of magnesium in a pill. In yet another preferred embodiment, an NMDA antagonist is combined with a GABA agonist and an appropriate dose of magnesium in the form of a pill. One of ordinary skill in the art will recognize that the composition of administration is not limited to a pill, but can also be a syrup, an elixir, a liquid, a tablet, a time-release capsule, an aerosol or a transdermal patch.

The ratio of acamprosate to magnesium can be varied to optimize the therapeutic synergy of the two ingredients. Magnesium N-aceytlhomotaurinate (Durlach, supra; 1980), with a Magnesium:acetylhomotaurinate ratio of approximately 1:20 by weight, does not optimize the therapeutic effect of the two components. At typical therapeutic dosages of acetylhomotaurinate, the amount of magnesium is too low to have therapeutically-relevant effects on glutamate transmission. In my experience, I have had excellent therapeutic results from combining a 2 gram daily dosage of acamprosate with 1 gram of elemental magnesium, given as a salt or chelate. This combination gives better relief of both TD and tics than 2 grams of acamprosate alone. I have also demonstrated (see case Report 5 below) that a single dose of 300 mg of magnesium will augment the therapeutic effect of a single 666 mg dose of acamprosate.

Allowing for variations in individual response, and variations in the intestinal absorption of both acamprosate and magnesium, I assert that the optimal ratio of mg: acetylhomotaurinate for an individual patient will be somewhere between 1:6 and 1:1. Lower ratios of magnesium to acamprosate are unlikely to boost the therapeutic effect of acamprosate significantly, and higher ratios than 1:1 are likely to produce magnesium toxicity (or at least GI intolerance) at a typical daily acamprosate dose of 2 grams. Although magnesium N-acetylhomotaurinate may be slightly more efficacious than calcium N-acetylhomotaurinate for treatment of tic disorders, in the present application we are effectively increasing the magnesium content of acamprosate and related compounds by administering magnesium ion (as a salt or chelate) in combination with a salt of N-acetylhomotaurinate, because there is a significant benefit to administering a higher ratio of magnesium to acamprosate than is present in the magnesium salt of acamprosate.

The effects of acamprosate are realized within hours after acamprosate administration. This observation is critically important to the hypothesized mechanism of action of acamprosate in the treatment of movement disorders. In 1997, Lidsky et al., (U.S. Pat. No. 5,602,150) described the use of taurine and taurine derivatives, including acamprosate, for the prevention of tardive dyskinesia in people taking neuroleptic drugs. In a rodent model, animals were given neuroleptics with or without taurine. Over several months, the animals receiving taurine were less likely to develop vacuous chewing movements (VCM), a movement disorder with similarity to TD in humans. The mechanism advanced to explain the effect was a long-term neuroprotective action of taurine, in which taurine blocked the long-term effect of glutamatergic overstimulation of striatal neurons. One of ordinary skill in the art would not expect an agent with neuroprotective activity against glutamate-induced excitotoxicity to necessarily be efficacious in the treatment of severe, established cases of movement disorder, and to produce benefit within hours of administration. Indeed, there are well-known situations in neurology where an effective preventive agent can actually aggravate an established case of the condition to be prevented. For example, dopamine agonist antiparkinson drugs may delay the onset of dyskinesia in patients treated with levodopa for Parkinson's disease. Yet, dopamine agonists can aggravate dyskinetic movements once they are established.

Magnesium ions also act as neuroprotective agents, particularly in models of neuronal injury mediated by NMDA-type glutamate receptors (Ema et al., *Alcohol*, February, 15;95-103, 1998; Greensmith et al., *Neuroscience*, October, 68:807-12, 1995; Heath et al., *J. Neurotrauma*, March, 15:183-9, 1998; Hoane et al., *Brain. Res. Bull.*, 45:45-51, 1998; Muir et al., *Magnes. Res.*, March, 11:43-56, 1998; Vanick'y et al., *Brain. Res.*, April, 789:347-50, 1998). However, the virtually immediate benefit of magnesium in the treatment of established movement disorders cannot be based on neuroprotection. Rather, immediate and direct effects of magnesium on neural transmission, including glutamatergic transmission, must be involved. In this connection, note that the dosages of magnesium used for neuroprotection in humans usually are well above the 1 gram per day that was the highest dose used here in the treatment of movement disorders.

Another aspect of the invention features a method of improving memory and cognition in humans with TD. A particularly preferred embodiment of the present invention is to develop methods for improving cognitive function in patients exhibiting TD, specifically to increase memory, span of concentration, and everyday functional performance in activities particularly dependent upon cognition. These improvements in function are measured both subjectively and objectively. The improvement in memory can be demonstrated by standard neuropsychological tests. The improvement in cognition is demonstrated by performance on neuropsychological tests, including without limitation, the Rey Auditory-Verbal Learning Test, and measurement of Choice Reaction Time, and by subjective indicators of performance at tasks highly dependent on cognitive processes. It will be obvious to one skilled in the art that numerous different neuropsychological tests could be employed to demonstrate that cognitive function improved in patients on a treatment regime that included acamprosate or any of the other above-described agents, including without limitation: other salts of acetylhomotaurine derivatives of homotaurine and acetylhomotaurine with similar pharmacodynamic effects on NMDA-glutamate and GABA neurotransmission, pro-drugs that are metabolized in the blood, liver, or brain to produce acetylhomotaurinate or derivatives with similar pharmacodynamic effects on NMDA-glutamate and GABA neurotransmission, and mixtures of two or more compounds that have, taken together, NMDA-glutamate antagonist and GABA agonist effects. All of these entities may also have neuroprotective actions against glutamate-induced excitotoxic damage, but their virtually immediate beneficial effect on the movement disorders and cognition, which is reversible if the medication is discontinued, cannot be due to such neuroprotective actions.

Another preferred embodiment of the present invention is the development of methods for improving tics and, as a consequence, reducing stigma and improving the quality of life for patients with tics or tic disorders such as TS. Yet another embodiment of the present invention is the development of methods for relieving blepharospasm, and the associated impairment visual function implied by frequent, forceful, involuntary eye closure. A final embodiment of the present invention provides methods of treating all focal dystonias, whether spontaneous or precipitated by exposure to neuroleptic drugs and other dopamine receptor blockers.

One of ordinary skill in the art will recognize that the present invention is not limited to a method of treating TD and other tic disorders with agents that reduce NMDA-type glutamate neurotransmission and increase GABA neurotransmission via direct effects on GABA and NMDA receptors. In addition to direct effects on receptor sites, the agents may modify NMDA-glutamate and GABA transmission through indirect effects on receptors (i.e., via pre-synaptic effects on neurotransmitter release, allosteric modulation of the receptor site, or effects on the intracellular response to the binding of the transmitter to the receptor), presynaptic effects on transmitter release, or any of a variety of mechanisms. It will be obvious to one skilled in the art that a range of derivatives and pro-drugs all should be therapeutically effective. Anything that shares the effects on glutamate and GABA transmission hypothesized to underlie the therapeutic effects of acamprosate is within the scope of the presently claimed invention. It does not matter how a drug, pro-drug or mixture thereof decreases NMDA-glutamate neurotransmission and increases GABA neurotransmission, only that it improves symptoms associated with TD and tics at tolerably non-toxic (ie., free from toxicity unacceptable side effects) doses.

As discussed previously, the inventive treatment can be used to treat any movement disorder characterized by any form of abnormal or involuntary movement. Furthermore, the inventive treatment may be used to improve or eliminate symptoms unrelated to movement that are consequences of the movement disorder, for example, cognitive dysfunction or abnormalities of motivation, mood, or impulse control. The latter include anxiety, depression, apathy, aggression, and obsessive compulsive behavior. The basal ganglia, including the striatum, are a point of intersection of motor, cognitive, and emotional circuits. Diseases of the basal ganglia frequently involve cognitive, emotional, behavioral, and motivational changes, as well as motor dysfunction. I expect that drug treatments effective for TD, tics, and other movement disorders might also alleviate some or all of the non-motor symptoms. In general, treatments for diseases of the basal ganglia do have non-motor effects. For example, dopamine agonist antiparkinson drugs not only increase the rate of movement of patients with Parkinson's disease, they also improve mental processing speed. When the addition of magnesium increases the effect of a drug treatment on the motor manifestations of a movement disorder, it may also increase the effect of that treatment on the non-motor manifestations.

The present invention will now be illustrated by the following non-limiting examples.

Case Report 1

A 45-year old woman had long-standing TD, originally induced by seven years exposure to amoxapine, an antidepressant drug with neuroleptic effects. The patient's irregularly-rhythmic movements consisted of forced eye blinking (blepharospasm), thrusting of the tongue forward and from side to side, tongue twisting, grimacing, shoulder shrugging, and tensing of the platysma muscles of the neck. (Had the patient's symptoms not been associated with neuroleptic exposure, a subset of her movements could be characterized as the Meige syndrome of oromandibular dystonia with blepharospasm). The patient is a semi-professional musician; the dyskinetic movements were accompanied by significant occupational disability, including difficulty reading music or text and difficulty playing woodwind instruments. Much of her reading impairment was due to frequent involuntary blinking and eye closure. She had impaired attention, concentration and memory compared with her performance before the onset of TD. She had significant fatigue, and usually required rest at some point during each day. The patient was diagnosed with TD by a board-certified neurologist with extensive experience in evaluating neuroleptic-induced side effects.

The patient's dyskinesia and dystonia worsened after the amoxapine was discontinued. Palliative treatment with alprazolam (an anxiolytic and GABA agonist via modulation; dosage 0.25 mg four times a day) and trihexyphenidyl (an anticholinergic antiparkinson drug that inhibits dopamine reuptake at synapses; dosage 2 mg twice a day) was prescribed by another physician. This combination produced minimal improvement. The patient began treatment with me in the winter of 1992 and was maintained on trihexyphenidyl for an additional 18 months. Trihexyphenidyl was then discontinued without a change in her involuntary movements. During 1993, alprazolam was increased to 0.5 mg four times a day, to treat mild symptoms of anxiety; the change in dosage had no detectable effect on the patient's involuntary movements. Treatment trials with buspirone, sertraline, verapamil, and vitamin E in 1992 either produced little benefit or were not tolerated at doses that only slightly reduced her involuntary movements. None of these drugs significantly improved the patient's everyday function, i.e., her performance at reading text or music, her stamina or her ability to concentrate. The first drug that provided significant and sustained benefits was nimodipine, a blocker of L-type calcium channels, that indirectly reduces dopaminergic activity (Bonci et al; *J. Neurosci.*, September 1, 18(17):6693-703 1998).

Beginning in 1993, nimodipine was administered at a dosage of 30 mg four times a day. Initially, her other medications were maintained unchanged. This regime reduced the patient's involuntary movements by about 50%. Unfortunately, the patient experienced adverse effects, including dizziness, lightheadedness, and palpitations. Also, she had no symptomatic improvement in cognitive function. There was a meaningful improvement in her ability to read and to play music. However, even with this improvement, she could read text or music for no more than 30 minutes at a time, before fatigue or blepharospasm prevented her from continuing.

In 1995, memantine came to my attention as a relatively non-toxic NMDA receptor antagonist. In view of my hypothesis about the pathophysiology of tardive dyskinesia, I thought that memantine might be beneficial in its treatment. Nimodipine was discontinued, and the patient was begun on memantine at a dosage of 10 mg twice a day. The involuntary movements of the patient's TD were reduced within 24 hours of administration of memantine, to a substantially greater degree than had been observed with nimodipine. Adverse effects included a sense of mild intoxication. Adjustments to the therapeutic regime were made such that the drug was reduced to 5 mg three times a day, with the result that the therapeutic benefits were maintained without perceptible side effects. In addition, the patient reported improved energy, attention, and concentration. Memantine was the patient's primary treatment for TD for the next 1½ years, until I became aware of acamprosate as an indirect NMDA antagonist with the added benefit of GABA agonism.

Prior to treatment with acamprosate, the patient's involuntary movements (on an optimal dose of memantine) consisted of eye blinking, puckering of the cheeks, writhing of the tongue and tensing of the platysma. These involuntary movements were usually mild and occasionally moderate in intensity. The movements had been substantially more severe in the past, but had been reduced significantly during the two-year course of treatment. Moreover, the patient's involuntary movements were accompanied by mild but definite cognitive impairment. The patient's most prominent cognitive symptom was difficulty sustaining concentration long enough to read more than a few pages of text.

The patient was taken off of memantine and treated with acamprosate at a dose of 333 mg four times a day. On acamprosate, the patient's involuntary movements (forced eye blinking (blepharospasm), thrusting of the tongue forward and from side to side, tongue twisting, grimacing, shoulder shrugging, and tensing of the platysma muscles of the neck) became imperceptible.

In addition, the patient's cognitive function improved significantly when measured both subjectively and objectively. On acamprosate, the patient was able to sustain concentration for prolonged periods. For example, she could now read a book for over an hour at a time, with good recall of what she had read. The patient's cognitive improvement was also assessed using formal neuropsychological measures. The patient was tested while on the drug, then taken off of the drug and tested two days later. On the drug, the patient was able to recall 13 of the 15 items after a short delay as well as 13 of the 15 items after a long delay, as measured by the Rey Auditory Verbal Learning Test. This was in comparison to the patient's ability while off the drug to recall only 7 of the 15 items after a short delay as well as 8 of the items after a long delay in tests performed. In addition, the patient was able to recognize all 15 of the items while on acamprosate but while off the drug (and while having been off of memantine for over 2 months) the patient could only recognize 10 of the items. The order of testing would give the advantage of familiarity to the off-drug condition. Nonetheless, the difference in favor of the on-drug condition was substantial.

Comparison with other neuropsychological tests demonstrated that the improved cognitive findings shown while the patient was on acamprosate were not explained by a nonspecific lack of effort or to concentration during off-drug condition. These additional tests, which reflect basic attention and psychomotor speed, showed that the patient actually had slightly better results off acamprosate. The tests showing such results included Simple Reaction Time, the Trail Making Test (both parts) and the Paced Auditory Serial Addition Test (PASAT). Choice reaction time, a test requiring both basic attention and concentration on a specific task that must be kept in mind, was slightly better on acamprosate, consistent with the hypothesis that general cognitive function, as opposed to simple attention, improves with acamprosate treatment.

The following tables report on the results of the neuropsychological tests (Drug I is memantine and Drug II is acamprosate):

TABLE 1

REACTION TIME, PSYCHOMOTOR SPEED, & MOTOR FUNCTIONING FOR DRUG I (MEMANTINE) AND DRUG II (ACAMPROSATE)

| TESTS | Feb. 23, 1994 | Feb. 23, 1996 ON DRUG I | Apr. 8, 1996 OFF DRUG I | Sep. 23, 1997 ON DRUG II | Sep. 25, 1997 OFF DRUG II |
|---|---|---|---|---|---|
| Simple Reaction Time[a] | | | | | |
| 1500 Green | NA | 212 msec | 332 msec | 261 msec | 234 msec |
| 1500 Red | NA | 224 msec | 276 msec | 264 msec | 241 msec |
| 500 Green | NA | 284 msec | 343 msec | 286 msec | 272 msec |
| 500 Red | NA | 266 msec | 382 msec | 272 msec | 237 msec |
| Choice Reaction Time[a] | | | | | |
| 1500 Green | NA | 365 msec | 542 msec | 408 msec | 442 msec |
| 1500 Red | NA | 422 msec | 643 msec | 379 msec | 435 msec |
| 500 Green | NA | 362 msec | 603 msec | 382 msec | 425 msec |
| 500 Red | NA | 421 msec | 557 msec | 426 msec | 413 msec |
| PASAT[a] | | | | | |
| 2.4 sec ISI errors | 17/49 | 13/49 | 15/49 | 4/49 | 0/49 |
| 2.0 sec ISI errors | 17/49 | 17/49 | 21/49 | 1/49 | 1/49 |
| 1.6 sec ISI errors | 11/49 | 21/49 | 22/49 | 11/49 | 4/49 |
| 1.2 sec ISI errors | 17/49 | 28/49 | 25/49 | 13/49 | 11/49 |
| Digit Symbol[b] | NA | 34 | 20 | NA | NA |
| Trails A | | | | | |
| Seconds[a] | 25" | 28" | NA | 20" | 16" |
| Errors[a] | 1 | 0 | NA | 0 | 0 |
| Motor Functions | | | | | |
| Grooved Functions sec.[a] DH = right | DH = 68" NDH = 82" | DH = 71" NDH = 70" | NA | DH = 61" NDH = 70" | DH = 59" NDH = 76" |
| Finger Tapping[b] | DH = 58.8 NDH = 41.6 | DH = 59.3 NDH = 48.5 | NA | NA | NA |
| Grip Strength[b] | NA | DH = 17.7 NDH = 21.7 | NA | NA | NA |

Note:
[a] lower score indicative of better performance
[b] higher score indicative of better performance

TABLE 2

EXECUTIVE, ATTENTION, VISUOCONSTRUCTIONAL & VISUAL MEMORY TASKS FOR DRUG I (MEMANTINE) AND DRUG II (ACAMPROSATE)

| TESTS | Feb. 23, 1994 | Feb. 23, 1996 ON DRUG I | Apr. 8, 1996 OFF DRUG I | Sep. 23, 1997 ON DRUG II | Sep. 25, 1997 OFF DRUG II |
|---|---|---|---|---|---|
| 1. Trails B | | | | | |
| Seconds[a] | 56" | 118" | NA | 43" | 39" |
| Errors[a,b] | 0 | 0 | NA | 0 | 0 |
| Verbal Fluency | | | | | |
| Letter (CFL)[b] | NA | Total = 70 Per = 2[b] | NA | NA | NA |
| Category (Animals)[b] | NA | Total = 25 Per = 0[b] | NA | NA | NA |
| Figural Fluency | | | | | |
| Unique Designs[b] | NA | 124 | 99 | NA | NA |
| Perseverations[a] | NA | 8 | 4 | NA | NA |
| 2. CPT - with conditions (Vigilance) | | | | | |
| Commission errors[a] | 0 | NA | NA | 0 | 0 |
| Omission errors[a] | 0 | NA | NA | 0 | 0 |
| Wrong[a] | 3 | NA | NA | 3 | 0 |
| Correct[b] | 50/50 | NA | NA | 100/100 | 100/100 |
| 3. Rey-Osterrieth Complex Figure | | | | | |
| Copy Presence & Accuracy[b] | NA | 20 | 17 | NA | NA |
| Copy Organization[b] | NA | 5 | 4 | NA | NA |
| Immediate Retention[b] | NA | −55 | −47.1 | NA | NA |
| Delayed Retention[b] | NA | −11.1 | 22.2 | NA | NA |

Note:
[a]lower score indicative of better performance
[b]higher score indicative of better performance

TABLE 3

MEMORY TESTING FOR DRUG I (MEMANTINE) AND DRUG II (ACAMPROSATE)

| TESTS | Feb. 23, 1994 | Feb. 23, 1996 ON DRUG I | Apr. 8, 1996 OFF DRUG I | Sep. 23, 1997 ON DRUG II | Sep. 25, 1997 OFF DRUG II |
|---|---|---|---|---|---|
| California Verbal Learning Test 16-items | | | | | |
| List A 1–5 total (80 max)[b] | NA | 53 | 40 | NA | NA |
| List A Trial 1[b] | NA | 7 | 6 | NA | NA |
| List A Trials[b] | NA | 13 | 9 | NA | NA |
| List B[b] | NA | 7 | 5 | NA | NA |
| Short-Delay Free Recall[b] | NA | 10 | 4 | NA | NA |
| Short-Delay Cued Recall[b] | NA | 13 | 9 | NA | NA |
| Long-Delay Free Recall[b] | NA | 12 | 7 | NA | NA |
| Long-Delay Cued Recall[b] | NA | 15 | 8 | NA | NA |
| Perseverations[a] | NA | 23 | 4 | NA | NA |
| Intrusions[a] | NA | 6 | 0 | NA | NA |
| Recognition Hits[b] | NA | 16 | 14 | NA | NA |
| False Positives[a] | NA | 3 | 0 | NA | NA |
| Rey-Auditory Verbal Learning Test 15-items | | | | | |
| List A 1–5 total (75 max)[b] | NA | NA | NA | 63 | 57 |
| List A Trials 1[b] | NA | NA | NA | 10 | 9 |
| List A Trials 5[b] | NA | NA | NA | 14 | 14 |
| List B[b] | NA | NA | NA | 8 | 9 |
| Short-Delay Free Recall[b] | NA | NA | NA | 13 | 7 |
| Long-Delay Free Recall[b] | NA | NA | NA | 13 | 8 |
| Perseverations[a] | NA | NA | NA | 5 | 0 |
| Intrusions[a] | NA | NA | NA | 0 | 3 |
| Recognition Hits[b] | NA | NA | NA | 15 | 10 |
| False Positive[a] | NA | NA | NA | 1 | 2 |

Note:
[a]lower score indicative of better performance
[b]higher score indicative of better performance In addition to increased cognitive ability, the patient also experienced an increase in stamina while taking acamprosate. Prior to beginning the acamprosate regime, the patient was fatigued by the end of the afternoon, requiring rest in order to be alert in the evening. This fatigue was significantly decreased while on the acamprosate regime, with a corresponding improvement in fatigue-related cognitive function. On acamprosate, the patient no longer needed to rest during the day in order to be alert and active during the evening.

To verify that the acamprosate was related to the patient's improvement in controlling movement disorders, cognitive function and stamina, the patient was removed from the acamprosate regime (as well as the memantine regime) for a period of four weeks. During the initial two-week period off acamprosate, the patient's involuntary movements gradually returned to her pre-acamprosate, off-memantine baseline. (While the patient's off-drug baseline was less severe than it was when she started on memantine two years earlier, her movements still were severe enough to interfere significantly with her everyday functioning.) From that point on, until acamprosate was re-instituted, she showed continual mild-to-moderate grimacing, tensing of the platysma, and forced eye closure. These involuntary movements worsened still further during periods of stress or fatigue. Moreover, the patient fatigued much more easily, to a degree that noticeably reduced her everyday functioning. Subjectively, the patient reported that concentration and memory both decreased.

Within two days of re-instituting treatment with acamprosate, the patient reported that her energy, stamina, concentration and memory had improved to the level experienced during her prior treatment with acamprosate. Two months after reinstitution of acamprosate, the patient's involuntary movements were absent except for very mild movements during times of stress.

In July 1998, this patient participated in a trial of magnesium supplementation as an adjunct to her treatment with acamprosate. During a 7 day baseline period on Campral Cacamprosate 333 mg four times a day plus alprazolam 0.25 mg four times a day, she noted six episodes of involuntary movements involving the face and neck, 2 moderate and 4 mild. For the following 10 days she added 250 mg three times a day of chelated magnesium. During the period of magnesium supplementation, she noted no involuntary movements.

Summary:

This example demonstrates that efficacious treatments for TD include memantine and acamprosate. Both treatments improve cognition and function as well as involuntary movements. Furthermore, both memantine and acamprosate relieve blepharospasm and Meige syndrome associated with more extensive tardive movement disorders. Finally, oral magnesium administration, given together with acamprosate at a ratio of 1:1.8 by weight, augments the therapeutic effect of acamprosate on the involuntary movements of TD.

Case Report 2

A 79-year old woman had long-standing TD following decades of treatment with the neuroleptic drug perphenazine. Her involuntary movements comprised bilateral chorea of the upper extremities, plus writhing of the tongue and tongue-biting. Both of the latter movements led to a very sore tongue. In addition, the patient experienced impairment of her short-term memory, which was attributed primarily to cerebrovascular disease.

Following treatment with memantine the patient's voluntary movements improved, but continued at a mild-to-moderate level. She also continued to have a sore tongue. Her cognitive symptoms did not improve. In addition to memantine, the patient regularly took antiepileptic drugs (gabapentin and lamotrigine), antiplatelet agents (aspirin and ticlopidine), as well as medications for hypertension, glaucoma and gastrointestinal symptoms (isosorbide mononitrate, metoprolol, timolol eye drops and olsalazine). These various drugs did not affect the patient's involuntary movements or cognitive symptoms; there was no noticeable change in either one at the time that each of the above-mentioned drugs was instituted.

The patient was placed on a treatment regime that included administration of 666 mg of acamprosate, three times daily. In this case, acamprosate was added to the patient's regimen, which continued to include memantine. Once the patient began taking acamprosate, her chorea and tongue-biting stopped completely, and the writhing movements of the tongue diminished substantially. Subjectively, the patient's memory improved to the extent that her long-term bridge partner stated that patient was noticeably better at remembering cards during the play of duplicate bridge. Despite past evidence from formal testing that the patient had impaired short-term memory, she performed normally on a two-sentence memory task, which involved testing the patient's recall ability using two sentences containing 13 separate details. On the two-sentence memory task, within three attempts the patient was able to recall 9 details and, using a multiple choice format, was able to recall a total of 11 details. Recall of 9 details on the third attempt would be normal for a middle-aged adult, let alone one in her 80s at the time of testing.

After a full year on memantine and acamprosate, the memantine was discontinued, with little change in the patient's symptoms. On acamprosate 666 mg three times a day, persistent symptoms included mild choreatic movements on the hands, mild involuntary movements of the tongue and jaw, and soreness of the tongue disproportionate to the visible involuntary movements.

Magnesium oxide, 250 mg three times a day, was added, each dose being taken together with the acamprosate. The movements and the tongue soreness improved further. The effect was definite: movements worsened when magnesium oxide was stopped and improved when it was restarted. After a month on magnesium, the dosage of acamprosate was increased to 666 mg four times a day, with 250 mg of magnesium oxide given together with each dose. On this regimen, the tongue movements and tongue soreness were completely eliminated. The only residual sign of TD was a mild degree of involuntary movement of the hands.

Summary:

Magnesium and acamprosate are both efficacious treatments of tardive dyskinesia when administered alone. More specifically, Case Report 2 demonstrates that acamprosate can improve both the involuntary movements associated with TD as well as the associated cognitive impairment, in a patient in whom memantine improves involuntary movements but not cognition. Furthermore magnesium, when administered with acamprosate can augment the efficacy of acamprosate in the treatment of TD. In this case, the combination of acamprosate and magnesium was efficacious at an magnesium:acamprosate ratio or 1:2.66.

Case Report 3

A 56-year old female professor of nursing had Parkinson's disease since her late 30s. The patient's Parkinson's disease was treated using levodopa/carbidopa and bromocriptine. The patient's profession required a high level of mobility and physical effort, but taking a sufficient dosage of the levodopa/carbidopa to allow adequate physical functioning at work resulted in the patient demonstrating severe peak-dose dyskinesia. The patient's manifestations of peak-dose dyskinesia consisted of writhing movements of the upper trunk, jerky lateral and rotatory movements of the neck, and chorea of both upper extremities. The patient accepted these involuntary movements because lower dosages of levodopa-carbidopa left her too rigid and hypokinetic to perform her job.

Prior to beginning treatment with acamprosate, the patient was on an antiparkinson treatment regime that consisted of 1 mg of pergolide three times a day, 5 mg of selegiline twice a day, and a combination of levodopa/carbidopa consisting of 550-600 mg of levodopa and 125-150 mg of carbidopa administered in divided doses. Concurrent medications that did not appear to affect her Parkinsonism or dyskinesia consisted of bethanechol, sertraline, carbamazepine, conjugated estrogens and medroxyprogesterone. (As with the additional medications mentioned in Case 2, there had been no noticeable change in the patient's Parkinsonism or dyskinesia after the introduction of each of the drugs listed.) The patient also received 10 mg of memantine three times a day, which had previously reduced her dyskinetic movements from severe to mild-to-moderate.

The patient began acamprosate as an addition to the anti-parkinson regime described above. Initially, the patient received 666 mg of acamprosate administered three times a day. Two weeks later the regime was adjusted such that the patient received 333 mg of acamprosate four times a day, taking one 333 mg pill with each daytime dose of 100 mg levodopa and 25 mg carbidopa. The patient's bedtime does of controlled-release levodopa-carbidopa (200 mg of levodopa and 50 mg of carbidopa) was continued, but were given without acamprosate. As soon as acamprosate was added to her regimen, the patient's severe peak-dose dyskinesia was reduced from moderate to mild intensity, and there were periods of up to two hours following each dose during which there was no dyskinesia at all. There was no decrease in the efficacy of the levodopa/carbidopa treatment of her hypokinesia and rigidity. On acamprosate, the patient experienced longer periods of good motor function, and she now had no periods at all where her motor function was inadequate for work or social activity. The reduction of the dyskinesia to a minimal level led to a substantial improvement in purposeful motor function of the upper extremities. To confirm that the patient's improvement was due to the administration of acamprosate, the patient was taken off the acamprosate. Within one day of stopping acamprosate, the patient's dyskinetic movements were as severe as they had been before acamprosate was first given. Upon re-instituting acamprosate, the patient experienced an immediate reduction in her dyskinetic movements. During the period off acamprosate, an attempt was made to replace acamprosate with baclofen (a GABA-receptor agonist) at a total daily dose of 30 mg, and then with baclofen at a total daily dose of 60 mg. These doses of baclofen were high enough to produce sedation and nausea, but they had no beneficial effect on the patient's dyskinesia. Additional improvement in the dyskinesia was subsequently obtained by replacing the pergolide with 1 mg. of pramipexole administered three or four times a day.

Several months later, magnesium (300 mg elemental magnesium, as a mixed chelate), was added to the regimen. It was taken three times a day, together with a one of the patient's regular doses of levodopa/carbidopa. There was an immediate reduction of the severity of dyskinesia. To establish whether the improvement was due to magnesium, the magnesium was stopped after several weeks. Within 2 days, the dyskinesia was definitely worse.

Summary:

Case Report 3 demonstrates that memantine and acamprosate can ameliorate the peak dose dyskinesia of treated Parkinson's disease. The efficacy of memantine and acamprosate in the treatment of the peak dose dyskinesia of Parkinson's disease can furthermore be augmented by coadministration of magnesium at a ratio of 1:1.48 by weight with acamprosate.

Case Report 4

A 37-year old man had extremely severe tardive dyskinesia and dystonia, as a result of over 15 years of treatment of bipolar disorder with lithium and an assortment of neuroleptics. His involuntary movements consisted of forced extension of the trunk, torsion of the lower legs, plantar flexion of the left foot, chorea of both arms, writhing of the tongue and grimacing. In addition, he had profuse sweating associated with the involuntary movements. To sit still in a chair, he had to forcefully grip both arms. In the chair, forced extension of the trunk practically lifted him out of the chair. His trunk and leg movements led to impaired balance, with a staggering gait and frequent near-falls. The continual severe movements were associated with impairment in concentration, which made his work less efficient. By virtue of talent and intelligence, however, he was able to work competitively as a software engineer. Because his bipolar disorder remained an active problem, continued neuroleptic treatment was necessary to maintain his mental health. He was maintained on lithium carbonate 300 mg three times a day, and risperidone 4 mg per day.

His movement disorder had been treated with benzodiazepines, anticholinergics, and dopamine agonists, all without meaningful benefit. He was then treated with acamprosate, first at a dosage of 333 mg three times a day, and then at a dosage of 666 mg three times a day. Acamprosate therapy was then augmented with magnesium sulfate, 300 mg three times a day. After several weeks, memantine 10 mg three times a day was added, but memantine was discontinued after a few days because it aggravated his movement disorder.

At one point during his treatment, the patient ran out of acamprosate, and was without it for three days. After 24 hours off acamprosate, his movement disorder returned to its (severe) baseline. 72 hours after resuming acamprosate, he regained his previous level of benefit.

The patient maintained a weekly log of symptoms, which is reproduced here as Table 4. The table shows that:
1) Acamprosate therapy was associated with improvement in all of his symptoms. For several of his symptoms—trunk movement, balance, and sweating 666 mg of acamprosate three times a day was more efficacious than 333 mg three times a day;
2) The addition of magnesium was associated with further improvement in several symptoms, i.e., movements of the face and tongue, neck and limbs;
3) Benefits of acamprosate increased with continued therapy;
4) Mental function, as indicated by subjective memory, improved along with the involuntary movements;
5) The addition of memantine aggravated the involuntary movements.

The patient's self-ratings understate the degree of improvement noted by three physicians (two neurologists and one psychiatrist) who examined the patient before and after treatment with acamprosate and magnesium. Before treatment, he was unable to sit in a chair without gripping the arms, writhing and rocking wildly. After treatment, he was able to walk across a room carrying a cup of coffee and not spilling any.

TABLE 4

PATIENT SELF-REPORT OF TD TREATMENT EFFECTS - CASE 4

Regimen

1. Acamprosate 333 mg three times a day
2. Acamprosate 666 mg three times a day
3. Acamprosate 666 mg three times a day + Magnesium sulfate, 300 mg three times a day
4. Acamprosate 666 mg three times a day + memantine 10 mg three times a day Symptoms Severity of face and tongue movements (10 is worst)
Severity of trunk movements (10 is worst)
Difficulty maintaining balance (10 is worst)
Sweating (10 is worst)
General well being (10 is best)
Memory and concentration (10 is best)
Side Effects (10 is none)

| Week Number | 0 | 1 | 2 | 3 | 4 | 5 | 6 | 7 | 8 | 9 |
|---|---|---|---|---|---|---|---|---|---|---|
| Regimen # Scale | baseline | 1 | 2 | 3 | 3 | 3 | 3 | 3 | 4 | 3 |
| Face/tongue | 7 | 5 | 7 | 6 | 4 | 2 | 3 | 3 | 6 | 4 |
| Neck | 7 | 7 | 7 | 6 | 5 | 5 | 4 | 3 | 6 | 4 |
| Trunk | 9 | 8 | 6 | 6 | 4 | 4 | 4 | 5 | 7 | 4 |
| Limbs | 8 | 6 | 7 | 6 | 4 | 2 | 3 | 5 | 7 | 4 |
| Balance | 7 | 7 | 5 | 6 | 6 | 4 | 4 | 4 | 6 | 4 |
| Sweating | 10 | 8 | 5 | 6 | 5 | 3 | 4 | 4 | 5 | 4 |
| Well-being | 7 | 8 | 8 | 8 | 9 | 9 | 9 | 9 | 7 | 9 |
| Memory | 8 | 9 | 9 | 9 | 9 | 9 | 9 | 9 | 9 | 9 |
| Side effects* |   | 7 | 7 | 9 | 9 | 9 | 9 | 9 | 7 | 9 |

*The only significant side effect was nausea and vomiting, which the patient experienced for the first day after starting acamprosate, the first day after increasing the dose of acamprosate, and the first day after adding memantine.

Summary:

Acamprosate is efficacious in the treatment of severe tardive dyskinesia and dystonia. Administration of magnesium with acamprosate enhances the therapeutic action of acamprosate in the treatment of severe TD and tardive dystonia. In the case reported, a good effect was obtained at a magnesium: acamprosate ratio of 1:2.22. Memantine, though often effective in the treatment of tardive dyskinesia, actually can aggravate it in certain individuals, such as the one described in Case 4. Treatment with acamprosate, with or without magnesium, can help alleviate a movement disorder that is aggravated by memantine. Additionally, this case report demonstrates that acamprosate, administered with or without magnesium, can relieve involuntary movements and other symptoms in patients with tardive movement disorders who continue to receive neuroleptics for their mental disorder.

Finally, Case 4 illustrates the point that a treatment that prevents the development of involuntary movements in an animal model of TD (i.e. memantine, see Andreassen et al. supra) may be of no benefit at all in treating humans with established TD.

Case Report 5

A 46 year old man had simple tic of the neck that involved forceful extension and rotation of the neck to the right. The tic had started in the context of therapy of depression with dextroamphetamine and pramipexole, a dopamine agonist drug. The tic occurred from 20-50 times per hour, with greater frequency when he was tired or under stress.

He was initially treated with 666 mg of acamprosate three times a day. Within 24 hours after the start of acamprosate therapy, the frequency and severity of the tic decreased dramatically, to a rate of less than 5 per hour. The patient often was free of tics completely for 2 to 3 hours after each dose of acamprosate, after which time the tic would very gradually return. The dose was then raised to 666 mg four times a day. On this dose, rates of more than 5 per hour occurred only under unusually stressful circumstances, and there were frequent tic-free periods of 4 hours or more. If acamprosate was omitted for a full day, the frequency of tics rapidly increased, to over 10 an hour. On a second day without acamprosate, the rate of tics was again over 20 per hour.

He then added chelated magnesium, at a dosage of 300 mg of elemental magnesium 3 times a day. With magnesium supplementation, the average tic frequency dropped to 6 hour or less. When 666 mg of acamprosate was given three times a day was given together with magnesium 300 mg three times a day, the usual tic-free period after each acamprosate dose increased from approximately 3 hours to approximately 5 hours.

Summary:

Acamprosate is efficacious in the treatment of a simple tic. The efficacy of acamprosate is enhanced by concurrent administration of magnesium. In this case, a good effect was obtained at a magnesium:acamprosate ratio of 1:2.22. By extension, acamprosate should be efficacious in the treatment of multiple tics and Gilles de la Tourette syndrome.

Case Report 6

A corresponding physician the United Kingdom recently reported to me on the treatment of a 47-year old woman with chronic schizophrenia and severe tardive dyskinesia. As in Case 1, the patient's involuntary movements included severe blepharospasm. In addition, she had involuntary rhythmic peri-oral movements, and chorea-like movements of both hands, like the patient in Case 2. She had no cognitive complaints, nor were cognitive abnormalities noted on routine psychiatric examination.

The patient had developed symptoms of paranoid schizophrenia in 1991, at age 40. The symptoms of psychosis included auditory hallucinations, bizarre delusions, and persecutory fears. She was started on oral haloperidol as an outpatient in July 1992 and had an acute dystonic reaction to the drug. She was subsequently hospitalized and stabilized on fluphenthixol decanoate, a depot neuroleptic given by intramuscular injections. Symptoms of TD developed in November, 1994, after 28 months of neuroleptic therapy. Switching the patient to an atypical neuroleptic, olanzapine or risperidone, did not eliminate her TD. Beginning in October 1997 the patient was treated for her schizophrenia with 2 mg of risperidone alone. On this modest dose of an atypical neuroleptic, she had severe symptoms of TD for which she eagerly sought treatment.

Memantine was started on Nov. 28, 1997 at a dose of 5 mg per day, increased after 7 days to 5 mg twice a day, and after another 7 days to 5 mg three times a day. After the first two weeks of memantine treatment (an on 5 mg twice a day) there was marked improvement in blepharospasm, though the movements started to return just before the second dose of the day was due. Two weeks later, on 5 mg three times a day, improvement was more sustained, with virtually no involuntary movements noted at the peak of a given dose of memantine, and only mild movements noted when a dose was due. Further dosage increases were attempted to completely abolish the involuntary movements. The maximum dose attainable without side effects was 10 mg twice a day; above that level the patient had complaints of dizziness. That dose of memantine was maintained through May of 1997. At that point, after 6 months of treatment with memantine, the patient had no blepharospasm or limb chorea, and only mild peri-oral movements.

In May 1998 the patient was started on acamprosate, in pursuit of complete elimination of her involuntary movements. Initially, acamprosate 333 mg three times a day was added to memantine 10 mg twice a day. With the addition of acamprosate, peri-oral movements were eliminated, and the patient was essentially free of involuntary movements. Memantine was discontinued in August 1998; the patient continued free of involuntary movements on acamprosate alone.

Summary:

Both memantine and acamprosate can alleviate the involuntary movements of TD in patients with chronic schizophrenia who continue to require neuroleptic therapy. Both drugs can relieve severe neuroleptic-induced blepharospasm. Acamprosate can relieve involuntary movements of TD that do not respond to memantine at doses tolerated by the patient. The response of drug-induced blepharospasm to these two agents suggests that memantine and acamprosate will be helpful in the treatment of idiopathic (spontaneous) blepharospasm. By extension, they can be expected to be useful in the treatment of other focal dystonias.

Discussion

The patients discussed in cases 1-6 above all exhibited a marked decrease in the frequency and severity of dyskinetic movements. Relief of symptoms began within 48 hours of administration of acamprosate, and, if a patient discontinued acamprosate, symptoms returned immediately. Those patients who previously exhibited cognitive disorders showed functionally significant improvement in cognitive function after beginning treatment with acamprosate (See cases 1, 2, and 4). This evidence supports my novel hypothesis that acamprosate, or a derivative with similar pharmacodynamic actions, will be helpful in the treatment of hyperkinetic movement disorders, including dyskinesias and dystonias, and the cognitive impairment associated with them. Acamprosate and similar drugs have simultaneous actions on GABA neurotransmission and NMDA-type glutamate neurotransmission that may be synergistic in regards to the therapy of hyperkinetic, dyskinetic and dystonic movement disorders. To the extent that other related compounds and mixtures of compounds have similar simultaneous effects upon GABA and glutamate neurotransmission, these related compounds may have the same or similar action on movement disorders and their associated cognitive impairments. Related compounds include, but are not limited to other salts of N-acetylhomotaurinate (e.g., magnesium N-acetylhomotaurinate), acetylhomotaurinate base, homotaurine, derivatives of these compounds, and pro-drugs metabolized in the liver, blood, or brain to yield acetylhomotaurinate or analogues with similar pharmacodynamic effects on GABA and NMDA-type glutamate neurotransmission. Additionally, any derivatives or pro-drugs that are easily absorbed after oral administration, or have a long half-life are particularly desirable.

Acamprosate also has benefits for treating hyperkinetic or dyskinetic movement disorders other than TD. Case 3 shows it is useful in alleviating the peak-dose dyskinesia of Parkinson's disease treated with levodopa. Case 1 shows acamprosate can be used successfully to treat blepharospasm (a focal dystonia) and Meige syndrome when these are associated with TD, and suggests that it can be used successfully to treat idiopathic blepharospasm and Meige syndrome. Case 4 suggests that acamprosate is efficacious in treating simple tics, and, by extension, multiple tics and Gilles de la Tourette syndrome. By extension, acamprosate will likely benefit patients with movement disorders not induced by neuroleptics, that show clinical symptomatology identical with those of a neuroleptic-induced (tardive) movement disorder. In particular, it may be efficacious in treating any of the focal dystonias, and in treating the involuntary movements of Huntington's disease.

As mentioned previously, magnesium ion is an NMDA receptor inhibitor, via blockade of calcium channels. I tested whether administration of elemental magnesium would enhance the efficacy of acamprosate in the treatment of simple tics. In Case 5, it is demonstrated that supplementing acamprosate with magnesium salts alleviates tics better than acamprosate alone. Therefore, magnesium may be combined with any other agents that increase GABA transmission and/or decrease NMDA-glutamate transmission to further suppress simple tics.

Both calcium acetylhomotaurinate and magnesium salts or chelates are safe medications when given in appropriate dosage. Because magnesium acetylhomotaurinate yields the same magnesium ions and homotaurinate ions when it dissociates in the GI tract as does the mixture of acamprosate and magnesium salts. I infer that magnesium acetylhomotaurinate will also be a safe medication. Therefore, magnesium N-acetylhomotaurinate would be a safe and effective drug, with potentially greater efficacy for movement disorders than acamprosate (calcium), because of the NMDA-receptor blocking action of the magnesium ion. However, as noted earlier, it does not have the ideal molar ratio of magnesium to N-acetylhomotaurinate for maximal therapeutic effect. Therefore, a magnesium salt or chelate combined with a salt of N-acetylhomotaurine or a derivative is likely to be more efficacious as a treatment for movement disorder. Magnesium ion combination with acamprosate and related compounds is likely to alleviate symptoms of various hyperkinetic, dyskinetic, and dystonic movement disorders, for example multiple tics, Tourette syndrome, tardive dyskinesia, and blepharospasm, and other focal dystonias.

It is likely that symptoms of the movement disorder associated with Huntington's disease will be relieved, at least in part, by acamprosate, alone or in combination with magnesium. Patients with Huntington's disease may show dyskinetic movements of the face and limbs resembling those of TD. Patients with Huntington's disease have a deficiency of GAD in the striatum, and are thought to suffer from neuronal death due to NMDA-receptor mediated excitotoxicity (D E Riley and A E Lang: *Movement Disorders*, in W G Bradley et al., editors, Neurology in Clinical Practice, Boston: Butterworth-Heinemann, 1991, p. 1568). These features of the disorder favor a positive response to acamprosate, a drug with joint actions on GABA and NMDA-receptors.

One aspect of the method of the invention features improvements in the cognitive disorder associated with TD. The improvement in cognition and everyday functional performance seen during the treatment of TD, makes acamprosate particularly attractive for patients with the cognitive impairment that frequently accompanies TD.

The relationship between tardive dyskinesia and cognitive impairment is not fully understood. It is known that pre-existing cognitive impairment increases the risk that TD will develop in the event a patient receives neuroleptics over a long-term period. It is also known that treated schizophrenics with TD are more likely to show progressive cognitive deterioration that those without TD. However, it is not known whether treatment of TD will ameliorate the cognitive deficits associated with TD. Cases 1, 2, and 4 discussed above suggest that at least some treatments of TD can ameliorate such cognitive deficits. The prior art does not report that the administration of acamprosate, when used as a treatment for alcoholism, improved the patients' cognition, I infer that the improvement in cognition seen in Cases 1, 2, and 4 was related to the improvement in their movement disorders. This is consistent with the well-established involvement of the basal ganglia in cognitive processes (Sano et al., Basal Ganglia Diseases, in Fugal et al., (eds.), Neuropsychiatry, Williams and Wilkins, 1996).

Moreover, the fact that acamprosate is also known as an agent used in the treatment of alcoholism makes acamprosate particularly suited for the treatment of patients who have a history of alcoholism in addition to a hyperkinetic movement disorder. Once such group is patients with schizophrenia and alcoholism (so called "dual diagnosis" patients), who have TD, for which alcoholism is a risk factor.

I claim:

1. A pharmaceutical composition comprising:
   (i) acamprosate; and
   (ii) an inorganic salt or chelate of magnesium;
wherein the ratio of acamprosate to the magnesium in said inorganic magnesium salt or chelate is between 1:1 and 6:1 by weight, and wherein the acamprosate and magnesium salt or chelate of magnesium are in a therapeutically effective amount for alleviating involuntary movement of tardive dyskinesia.

2. The composition of claim 1, wherein the inorganic salt or chelate of magnesium comprises magnesium chloride, magnesium oxide, magnesium sulfate, and magnesium chelated with an amino acid.

3. The pharmaceutical composition of claim 1, wherein the composition comprises an inorganic salt of magnesium.

4. The pharmaceutical composition of claim 1, wherein the composition comprises a chelate of magnesium.

5. The pharmaceutical composition of claim 1, wherein the acamprosate is in an amount of 333 mg to 666 mg.

6. The pharmaceutical composition of claim 1, wherein the acamprosate is in an amount of 333 mg.

7. The pharmaceutical composition of claim 1, wherein the acamprosate is in an amount of 666 mg.

* * * * *